US007745166B2

(12) United States Patent
Lobel et al.

(10) Patent No.: US 7,745,166 B2
(45) Date of Patent: Jun. 29, 2010

(54) HUMAN LYSOSOMAL PROTEIN AND METHODS OF ITS USE

(75) Inventors: Peter Lobel, Highland Park, NJ (US); David Sleat, Scotch Plains, NJ (US)

(73) Assignee: University of Medicine and Dentistry of New Jersey, Newark, NJ (US)

(*) Notice: Subject to any disclaimer, the term of this patent is extended or adjusted under 35 U.S.C. 154(b) by 13 days.

(21) Appl. No.: 12/175,427

(22) Filed: Jul. 17, 2008

(65) Prior Publication Data

US 2009/0075315 A1 Mar. 19, 2009

Related U.S. Application Data

(60) Continuation of application No. 11/788,045, filed on Apr. 18, 2007, which is a continuation of application No. 10/643,233, filed on Aug. 18, 2003, now abandoned, which is a division of application No. 09/851,847, filed on May 9, 2001, now Pat. No. 6,638,712, which is a division of application No. 08/931,608, filed on Sep. 16, 1997, now Pat. No. 6,302,685.

(51) Int. Cl.
*C12Q 1/37* (2006.01)
(52) U.S. Cl. ........................................ 435/23
(58) Field of Classification Search ................ None
See application file for complete search history.

(56) References Cited

OTHER PUBLICATIONS

Sharp et al., "Loci for classical and a variant late infantile neuronal ceroid lipofuscinosis map to chromosome 11p15 and 15q21-23," *Human Molecular Genetics*, 6:591-595 (1997).
Lerner et al., "Isolation of a novel gene underlying Batten disease, CLN3," *Cell*, 82: 949-957 (1995).
Ivy et al., "Protease inhibitor as a model for NCL disease, with special emphasis on the infantile and adult forms," *American Journal of Medical Genetics*, 42: 555-560 (1992).
Ashizawa et al., "Diagnostic value of ophthalmologic finding in myotonic dystrophy: Comparison with risks calculated by halotype analysis of closely linked restriction fragment length polymorphisms," *American Journal of Medical Genetics*, 42: 55-60 (1992).
Sleat et al., "Glucosidase and N-acetylglucosamine-6-sulphatase are the major mannose-6-phosphate glycoproteins in human urine," *Biochem.*, 324: 33-39 (1997).
Ezaki et al., "Specific delay in the degradation of mitochondrial ATP synthase subunit c in late infantile neuronal ceroid lipofuscinosis is derived from cellular proteolytic dysfunction rather than structural alternation of subunit c," *Journal of Neurochemistry*, 67: 1677-1687 (1997).
Ivey et al., "Inhibitors of lysosomal enzymes: Accumulation of lipofuscin-like dense bodies in the brain," *Science*, 226: 985-987 (1994).
Davidson et al., "Recombinant adeno-associated virus type 2, 4, and 5 vectors: Transduction of variant cell types and regions in the mammalian central nervous system," *Proc. Natl. Acad. Sc.*, 97: 3428-3432 (2000).
Xiao et al., "Gene transfer by adeno-associated virus vectors into the central nervous system," *Exp. Neurol.*, 114: 113-124 (1997), Abstract.
Clark et al., "Gene transfer into the CNS using recombinant adeno-associated virus: Analysis of vector DNA forms resulting in sustained expression," *J Drug Target*, 7: 269-283 (1999), Abstract.
Passini et al., "Intracranial delivery of CLN2 reduces brain pathology in a mouse model of classical late infantile neuronal ceroid lipofuscinosis," *The Journal of Neuroscience*, 26: 1334-1342 (2006).
Sondhi et al., "AAV2mediated CLN2 gene transfer to rodent and non-human primate brain results in long-term TPP-1 expression compatible with therapy for LINCL," *Gene Therapy*, 12: 1618-1632 (2005).
Haskell et al., "Viral-mediated delivery of the late-infantile neuronal ceroid lipofuscinosis gene TPP-1 to the mouse central nervous system," *Gene Therapy*, 10: 34-42 (2003).
Hackett et al., "Safety of direct administration of AAV2$_{cu}$hCLN2, a candidate treatment for the central nervous system manifestations of late infantile neuronal ceroid lipofuscinosis, to the brain of rats and nonhuman primates," *Human Gene Therapy*, 16: 1484-1503 (2005).
Cabrera-Salazar et al., "Timing of Therapeutic Intervention Determines Functional and Survival Outcomes in a Mouse Model of Late Infantile Batten Disease," *Molecular Therapy*, 15(10): 1782-1788 (2007).
Worgall et al., "Treatment of Late Infantile Neuronal Ceroid Lipofuscinosis by CNS Administration of a Serotype 2 Adeno-Associated Virus Expressing CNL2 cDNA," *Human Gene Therapy*, 19: 1-12 and 12A-F (2008).

*Primary Examiner*—Jon P Weber
*Assistant Examiner*—Satyendra K Singh
(74) *Attorney, Agent, or Firm*—Jones Day

(57) ABSTRACT

The gene associated and causative of classical late infantile neuronal ceroid lipofuscinosis (LINCL), CLN2, has been identified and characterized. The translation product of this gene is a novel protease and a deficiency in this activity results in LINCL. Identification of CLN2 will not only aid in the prevention of LINCL through genetic counseling but provides strategies and test systems for therapeutic intervention. In addition, further characterization of this previously unknown lysosomal enzyme may provide useful insights into other more common human neurodegenerative disorders. Finally, the utility of a general approach for determining the molecular bases for lysosomal disorders of unknown etiology has been demonstrated.

5 Claims, 8 Drawing Sheets

FIG. 3A

```
  1 CGCGGAAGGGCAGAATGGGACTCCAAGCTGCCTCTAGGGCTCTTTGCCCTCATCCTTCTGGCAAATGCGAGTTACAGCCCGGAGCCCG
                 M  G  L  Q  A  C  L  L  G  L  F  A  L  I  L  L  S↙G  K  C  S  Y  S  P  E  P  D

91 ACCAGCGGAGACGCTGCCCCCAGCTGGGTCCTGGGTGTCCCTGGACCGTGAGGAAGAGCTGAGTCTCACTTTGCCCTGAGACAGC
     Q  R  R  T  L  P  P  G  W  V  S  L  G  R  A  D  P  E  E  L  S  L  T  F  A  L  R  Q  Q

181 AGAATGTGGAAGACTCTCGGAGCTGGTGCAGGCTGTGTCGGATCCAGCTCCTCAATACGGAAAATACCTGACCCTAGAGAATGTGG
     N  V  E  R  L  S  E  L  V  Q  A  V  S  D  P  S  S  P  Q  Y  G  K  Y  L  T  L  E  N  V  A

271 CTGATCTGGTGAGGCCATCCCTGACCCTGAGCATGCTGGCTGCAAAATGGCTTCTGGCAGCCGGAGCCCAGAAGTGCCATTCTGTGATCA
     D  L  V  R  P  S  P  L  T  L  H  T  V  Q  K  W  L  L  A  A  G  A  Q  K  C  H  S  V  I  T

361 CACAGGACTTTCTGACTTGCTGGCTGTAAGTCCGAGACATCCGAGACAAGAGCTGCTCCCTGGGGCTGAGTTTCATCACTATGTGGGGAGACCTA
     Q  D  F  L  T  C  W  L  S  I  R  Q  A  E  L  L  L  P  G  A  E  F  H  H  Y  V  G  G  P  T

451 CGGAAACCCATGTGTAAGTCCCCACATCCCTACCAGCCTTCCACAGAGCCCTGCCCCATGCCAGTCTGGAGCCTGTAGCCGTCATCTCTGTGATCC
     E  T  H  V  V  R  S  P  H  P  Y  Q  L  P  Q  A  L  A  P  H  V  D  F  V  G  G  L  H  H  F

541 TTCCCCAACATCATCCTGAGGCCAACAGACGTTGGGGCCCAAGTAACAGCAGCAAGCCAAGCTGTGCCCAGTTCCTGGAGCAGTATTTCC
     P  P  T  S  S  L  R  Q  R  P  E  P  Q  V  T  G  T  V  G ↙L  H  L  G  V  T  P  S  V  I  R

631 GTAAGCGATACAACTTGACTTCACAAGA│D│GTGGGCAGTGGCACCTCCAACAACAGCCAAGCCTGTGCCCAGTTCCTGGAGCAGTATTTCC
       V  G  S  G  T  S  N  N  S  Q  A  C  A  Q  F  L  E  Q  Y  F  H
     │K  R  Y  N  L  T  S  Q│ D
                     *

721 ATGACTGGACCTGGCTCAGTTGACGCATGCGCCTCTAGAATGCGGCTAGATGTGCAGTACCTGATGAGTGCTGGAGCAATCAGTACCGTGTGGTTGGACAACAGGGC
     D  S  D  L  A  Q  F  M  R  L  F  G  G  N  F  A  H  Q  A  S  V  A  R  V  V  G  Q  Q  G  R

811 GGGGGCCGGGGCCGGGATTGAGGCTAGTCTAGATGTGCAGTACCTGATGAGTGCTGGAGCAATCAGTACCGTGTGGTTGGACAACAGGGC
     G  R  A  G  I  E  A  S  L  D  V  Q  Y  L  M  S  A  G  A  N  I  S  T  W  V  Y  S  S  P  G

901 GCCGGCATGAGGAGGACAGAGGAGCCCTTCCTGCAGTGGCTCATGATGCTCAGTAATGAGTCAGCCCTGCCACATGTGCATACTGTGAGCTATG
     R  H  E  G  Q  E  P  F  L  Q  W  L  M  L  S  N  E  S  A  L  P  H  V  H  T  V  S  Y  G
```

FIG. 3B

```
 991 GAGATGATGAGGACTCCCTCAGCAGCGCCTACATCCAGCGGGTCAACACTGAGCTCATGAAGGCTGCTGCGGGTCTCACCCTGCTCT
       D  D  E  D  S  L  S  S  A  Y  I  Q  R  V  N  T  E  L  M  K  A  A  A  R  G  L  T  L  L  F
1081 TCGCCCTCAGTGACAGTGGGGCCGGGTGTTGGTCTGTCTCTGAAGACACCAGTTCGCCCTACCTTCCCGCCTTCCGCCTCCTATGTCA
       S  A  S  G  D  S  G  A  G  C  W  S  V  S  G  R  H  Q  F  R  P  T  F  P  A  S  S  P  Y  V  T
1171 CCACAGTGGGAGGCACATCCTTCCAGGAACCTTTCCTCATCACAAATGAAATTGTTGACTATATCAGTGGTGGCTTCAGCAATGTGT
       T  V  G  G  T  S  F  Q  E  P  F  L  I  T  N  E  I  V  D  Y  I  S  G  G  F  S  N  V  F
1261 TCCCACGGCCTTCATACCAGGAGGAAGCTGTAACAAAGTTCCTGAGCTCTAGCAGTCCCCACCTGCCACCATCCAGTACTTCAATGCCAGTG
       N  P  R  P  S  Y  Q  E  E  A  V  T  K  F  L  S  S  P  H  L  P  P  S  S  Y  F  N  A  S  G
1351 GCCGTGCCTACCCAGATGTGGCTGCACTTTCTGATGGCTACTGGGTGGTCAGCAACAGAGTGCCATTCCATTGGGTGTCCGAACCTCGG
       R  A  Y  P  D  V  A  A  L  S  D  G  Y  W  V  V  S  N  R  V  P  I  P  W  V  S  G  T  S  A
1441 CCTCTACTCCAGTGTTCGGTGTTGGGGGATCCTATCCTTGATCAATGAGCACAGATCCTTAGTGCGCCCCCTTGCTTTCTCAACCCAA
       S  T  P  V  F  G  G  I  L  S  L  I  N  E  H  R  I  L  S  G  R  P  P  L  G  F  L  N  P  R
1531 GGCTCTGTGTCCTGGGTGGACCCGGGCCAGGACTCTTGATGTAACCGTGCCTGGCTGCCATGAGTCCTGCTTGGATGAAGAGAGGGCCAGGGTT
       G  S  G  P  G  W  D  P  V  T  G  W  G  T  P  N  F  P  A  L  R  C  H  E  S  C  L  D  E  E  V  E  G  Q  G  F
1621 TCTGCTCTGTGCTGGGATCCTGTAACAGGCTGGGAACACCCAACTTCCCAGCTTGCTGAAGACTCTACTGAAGCCCTGCGAACCCTCA
       C  S  G  P  G  W  D  P  V  T  G  W  G  T  P  N  F  P  A  L  R  K  T  L  L  N  P  *
1711 TTCCTATCAGGAGAGATGGCTTGTCCCCTGCCCAGTCAGTTCAGTCAGTTCAGTTGAAGCCCTGCTGAACCCTCA
1801 ACTATTGACTGCTCAGACAGCTTGACTGTGAGCTTGAGCTTGAGCTTGACTTGTGAACCTACCTCCAACCTGACTTGAGCTTGACTTCCCAACCTGACTTGAGCTTGACTGCTCCATGCTCCATCATACT
1891 CAGGTCTCCTACTCCTGCCTTCAAAGGCTTCTTGCCTTAGATTCCCTCAATAAGATGCTGTAACTAGCATTTTTGAAATGCCTCCTCCGCATCCATCTCATCTTCTC
1981 TTTTCATCAGGCTTTCAAAGGGTTGTATACAGACTCTGTGCACTATTCACTTGATATTCATTCCCAATTCACTCACTGCAAGGAGACCT
2071 CTACTGTCACCGTTACCTCCTTCTCCCTCTTCCTCCTTCCTTACTTCCTTCCTCCTAAGCATCTCAGAGAAACAATGCCTCCAGTGCATACTCTTGCATACTCTTGCTTAACTCTCTCAGTGCTCTAACTCTCTTGTCTTCCTTATGGCCTTTCC
2161 ATCATAGTTGCACTCCATCCCTCTTCCTCCTTCATTGTTACTTTGTAGATTTTGTGCTCTCCATTGCTCCATTTGCTCTCCATTGCTCTCCAGTTGCTCTCCAGTTGCTTACTCAGTTACTCAGTTCATTTGCTCTCTCATCAATTTCTGCTT
2251 CTTCATGAAATGCTGACCTGACTGAGAATGCTGACCTGACTGTTACTCAGTTTACTCAGTTACTCAGTTACTCAGTTACTCAGTTACTCAGTTACTCAGTTACTCAGTTACTCAGTTCATTGTCCCCTGAACAAATCACTGACATC
2341 TACAACCATTACCATCTCACTAAATAGACTTTCTATCCAATAAATGATTGATACCTCAAA
```

FIG. 3C

```
2401 TGTAAGATGGTGATACTCAACATTTCATCGTCCACCTTCCCAACCCAAACAATTCATCTCGTTTCTTCTTGGTAAATGATGCTATGC
2491 TTTTCCAACCAGCCAGAAACCTGTGTCATCTTTCACCCCACCTTCAATCAACAAGTCCTCAATCAACAAGTCCTACTGACTGCACAT
2581 CTTAAATATATCTTATCAGTCCACAAGTCCTTCCAAGTATATCCCAAGTATATCTAGAACTTATCCACTTATATCCCCACTGCTACT
2671 ACCTTAGTTTAGGGCTATATTCTCTTGAAAAAAGTGTCCTTACTTCCTGCCAATCCCAAGTCATCTTCAGAGTAAATGCAAATCCC
2761 ATCAGGCCACTTGGATGAAAACCCTTCAAGGATTACTGAAATTCAGGCTTTCCCCTCCASCCCCCAATCATAGCTCACAAACTTC
2851 CTTGCTATTTGTTCTTAAGTAAAAATCATTTTCCTCCTCCCCAAACCTCAGTTCAGAGAACTCTCACTCTTGCTCAAGCTGTTCCGTCC
2941 CCTTACCACCCCTGATACAACTGCCAGGTTAATTCTGCAAGAATCCTAGATTTCTGAAGACTCAGTTCAGAAGTCACCTTCTTTCGTTGAATGTTTGA
3031 TTCCCTGAGGCTACTTATTTGGTATGGCTGAAAAATCCTAGATTTCTAAACAAAACCTGTTTGAATCTTGGTTCTGATATGGACTAG
3121 GAGAGAGACTGGGTCAAGTAAGCTTATCTCCCTGAGGCTGTTCCTCGTCTGTTAAGTGTGAATATCAATACCTGCCTTTCATATCACC
3211 AGGGAATAAAGTGGAATAAATGTTGATAACAGTGCTTGGCACCTGGAAGTGGCAGATGTTAACGCCCTTCCTCCCTTGCACTGCGCC
3301 CCCTGTGCCTACCTCTAGCATTGTAACGACCACAGTATTGAAATGCCAGTTTACTTGTCTGCCTTTCCTTTCCAAGACCGTTGGTGCC
3391 TAGAGGACTAGAATCGTGTCCTATTTAACTTTGTGTTCCCAGTCCTAGCTCAGGAGTCCTAGCTCAGGAGTTGGCAAATAAGAATAAATGTCTGCTACACCG
3481 AACAAA
```

/AAAAAAAAAAA

FIG. 4A

```
CLN2    1   ..........................MGSLQACLLGL.FAILLSGKCSYSPEPPQR.................
PsCP    1   MKSSAAKQTV.CLNRYAV.VALPLAIASFAAFGASP.....................................
XaCP    1   ..........AKIEKTATVAIAILAAMSSLSAEAEDAWVSTHTQAAMSPPASTQVLAASTSRATTGNPATLNMTGSPRID

CLN2   37   ..SLGRADPEEPLSITFALRQQNVERLSELVQAVSDPSSPQMFKVLTENVADLVRPSPLTLEFVQKMLLAAGQKCESV
PsCP   59   ARPLLELARGETAHIIVVSLKIRDEAQLKQLAQAVNQPGNAQFGKFLKRRPFLSQFAPTRAQVDAVVAHLRKNGFVNIE.M
XaCP   71   GAAVTALEADHPLHVEVALKLRNPDALQTFLAGVTTPGSALFGKFLTPSQFTERGFTPSQVDAVVAHLQQAGETNIE.M

CLN2  115   ITQDFFLTCWLSIRQAELLLPGAEFHHVGGPTETHVVRSPHPYQLPQALAPHDPVGGLHHFPPTSSLR....QRPEPQVT
PsCP  138   VPNRLLISADGSAGAVTKAAFNTPLVRYDLNGKAGYA....NTKPAQVPDLGEIVGSVLGLQNVTRABPLKVGERSAAK..
XaCP  150   APNRLLISADGFAGAATNGFRTSIKRFSANGRFFA..NDAPALVPASLGDSVNAVLGLQNVSKHLEHVTHPEDVTGP

CLN2  192   GTVGLHTGVTPSVIRKYNLTSQDVGSGTSNNSQACAQFLEQYFHDSDEAQFMRLFGGNFAHQASVARVGQQGRGRAGI
PsCP  214   ...FLAAGTAKGHNPTEFPTTYDASSAPTANTHVGIITHIGSVSQTLDDIQQFTSA...NGLASVNTQTIDGSSNGDY
XaCP  228   GFNVGTPAAAVAAHHPDEFRAIYGSSSLPFAINTAVGITWGSLTPAILNTAVGTVDINSETSG...AGLAFNSTITKVGS..GFF

CLN2  272   ..............FASLDVQYIM.SAGANISTWV.VLSSPGRHFSQEPFLQVTMLLSNESALPH...VETVSFDDE.DSLSSAY
PsCP  287   SDPQGGSEWDLDSQSFVGSAGGAVDQLFYMADQSASGNTGLTQA...ENDAVSPNVAKVINVSLGMVCEADANADFT
XaCP  304   ANDPDSNGEWSLDSQDIVGTAGG.VKQLIFYISANGGLTPAGITASYNRAVTDNIAKIINVSLGEDZTAPAQQSGI

CLN2  337   ........IDRVNTELMKAAAARGLTLLFASGDSGA.........GCWSVSGGR...........HQFRPTEPASSPYVTVGGTSFQEPFL
PsCP  362   LQAEDRIFATAAAGQTFSVSSGDEGVYE........CNNRGYPDGSF..YSVSWPASSPNVIAVGTTLYITSA
XaCP  383   QAADALFQA.QGQTFSIAISGDAGVYDPWSTDPTSGSPGYVANSAGTVKIDLTHYSVSEPASSPYVIQVGGTTL.SFSG
```

FIG. 4B

```
CLN2  399  INEIVDYISGGGESNVTFPRPS.......YQEEAVTKFLSSPHLPPSSYFNASGRAYPDV...AALSPGYWVVSNRVPIP
PsCP  427  GAYS.NETVWNEGL........DSNGKIWATGGYSVTESKPSWQSWVSTPGRRLLPDISFDAAQGTGALIYNY..GDLQ
KaCP  462  TFNS.GETVWNEGLSAIAPSQGDNNQRLWATGGGVSLYEAAPSWQSSVSS.STKRVGPDLAFDAASSEGALIVWN.GSTE

CLN2  470  WVSGTSASTPMFGGILSLINEHRILSGRPPEGFLNPRLKQBGAG...LFDVTRGCHESCLDEEVEGQCSGPGWDPVT
PsCP  497  DIGGTSLASPIFVGLWARLQS.......ANSNSLGFPAASFYSAISSTPSIVHDVTSG.......NNGYGGYNAGTGWDIPT
KaCP  539  QVGGTSLASPIFVGAFARIES.......AANNAIGFPASKFYQAFPTQTSLLHDVISG.......NNGYDSHFYPANGPDPAI

CLN2  547  SWGIPNFPALIKHLLNP......
PsCP  567  PWGSLDI.AKLSAVTRSNGFGH......
KaCP  609  GFGSPDI.GFLAVTAQANWTGGGGGST
```

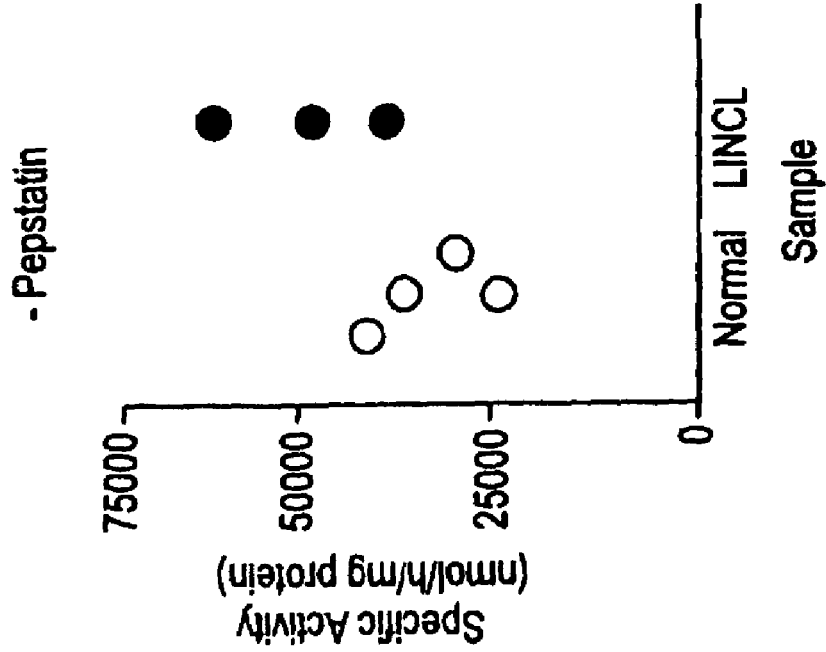
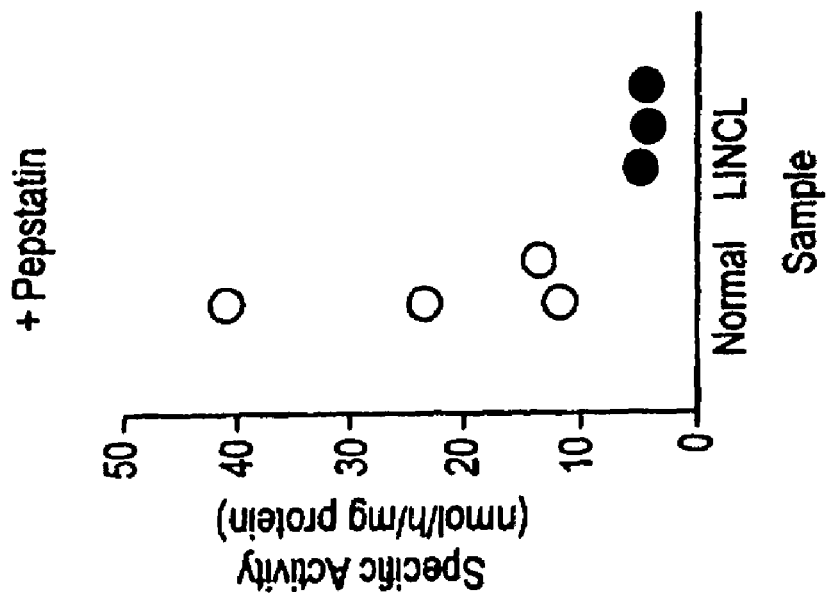

HUMAN LYSOSOMAL PROTEIN AND METHODS OF ITS USE

This application is a continuation of co-pending application Ser. No. 11/788,045, filed Apr. 18, 2007, which is a continuation of application Ser. No. 10/643,233, filed Aug. 18, 2003, now abandoned, which is a divisional of application Ser. No. 09/851,847, filed May 9, 2001, now U.S. Pat. No. 6,638,712, which is a divisional of application Ser. No. 08/931,608, filed Sep. 16, 1997, now U.S. Pat. No. 6,302,685, all of which are incorporated herein by reference in their entireties.

The research leading to the present invention was supported, in part, by National Institutes of Health Grants DK45992 and NS30147. Accordingly, the Government may have certain rights in the invention.

FIELD OF THE INVENTION

The present invention relates to the identification of a gene (CLN2) which, when mutated, results in the neurodegenerative disease classical late infantile neuronal ceroid lipofuscinosis (LINCL). CLN2 encodes a pepstatin-insensitive carboxyl protease which is a 46 kDa lysomal protein that is absent or mutated in LINCL. Thus, the invention provides the protease (CLN2), nucleic acids encoding CLN2, oligonucleotides specific for such nucleic acids, antibodies to CLN2, and methods for restoring the activity of CLN2 to ameliorate the symptoms of LINCL. Various diagnostic and therapeutic aspects of the invention particularly relate to detection and treatment of LINCL.

BACKGROUND OF THE INVENTION

The neuronal ceroid lipofuscinoses (NCLs) are a group of closely related hereditary neurodegenerative disorders which affect infants, children and adults, and which occur at a frequency of between 2 and 4 in 100,000 live births (1, 2). Most forms of NCL afflict children and their early symptoms and disease progression tend to be similar. Initial diagnosis is frequently based upon visual problems, behavioral changes and seizures. Progression is reflected by a decline in mental abilities, increasingly severe and unbeatable seizures, blindness and loss of motor skills while further progression can result in dementia or a vegetative state. There is no effective treatment for NCL and all childhood forms are eventually fatal. Several forms of NCL are differentiated according to age of onset, clinical pathology and genetic linkage. These include infantile NCL (INCL. CLN1), classical late infantile NCL (LINCL. CLN2), juvenile NCL (JNCL, CLN3) adult NCL (CLN4), two variant forms of LINCL (CLN5 and CLN6) and possibly other atypical forms (1,3). The molecular bases for two of these forms of NCL have recently been identified by positional cloning. Mutations in palmitoyl protein thioesterase (PPT), which removes the lipid moiety from acylated proteins, results in INCL (4). JNCL results from mutations in the CLN3 gene product, a 48 kDa protein of currently unknown function (5). The identity of the molecular lesion in LINCL has remained elusive although the disease gene has recently been mapped to chromosome 11p15 by genetic linkage analysis (3). There are reasons, however, to suspect that the CLN2 gene product could have a lysosomal function. First, LINCL, like other forms of NCL, is characterized by an accumulation of autofluorescent lysosome-like storage bodies in the neurons and other cells of patients. Second, a number of other related neurological disorders are caused by lysosomal deficiencies, e.g. PPT in INCL, neuraminidase in sialidosis and β-hexosaminidase A in Tay-Sachs disease. Third, continuous infusion of leupeptin and other lysosomal protease inhibitors into the brains of young rats induces a massive accumulation of ceroid-lipofuscin in neurons that resembles NCL (6,7).

Thus, there is a need in the art to identify and characterize the CLN2 gene and its gene product (CLN2).

There is a further need to develop diagnostic and therapeutic applications, based on CLN2, for prenatal testing and treatment of LINCL.

The present invention addresses these and similar needs in the art.

The citation of any reference herein should not be construed as an admission that such reference is available as prior art to the invention.

SUMMARY OF THE INVENTION

Classical late infantile neuronal ceroid lipofuscinosis (LINCL) is a fatal neurodegenerative disease whose defective gene (CLN2) has remained elusive. The molecular basis for LINCL has been determined here using an approach that should be applicable to other lysosomal storage diseases. Using the mannose 6-phosphate carbohydrate modification of newly synthesized lysosomal enzymes as an affinity marker, a single lysosomal enzyme was identified which is absent in LINCL. This protein was purified, cloned and sequenced. Sequence comparisons and activity (measurements suggest that the CLN2 protein is a novel pepstatin-insensitive lysosomal peptidase. In patients, a number of mutations in the gene encoding this protein were found, confirming it as CLN2.

A biochemical approach, which relies upon the fact that newly synthesized soluble lysosomal enzymes contain a modified carbohydrate, mannose 6-phosphate (Man 6-P), was used to identify a protein that is deficient in LINCL. Man 6-P functions as a targeting signal in vivo as it is recognized by Man 6-P receptors (MPRs) which direct the intracellular vesicular targeting of newly synthesized lysosomal enzymes from the Golgi to a prelysosomal compartment (8). Purified cation-independent MPR can be used as an affinity reagent for the detection of immobilized Man 6-P glycoproteins in a Western blot-style assay or can be coupled as a affinity chromatography reagent for the purification of Man 6-P glycoproteins (9, 10, 11). Thus, a preferred embodiment of the invention includes purification of lysosomal proteins by affinity chromatography using immobilized MPR, followed by peptide sequence analysis, and then use of this sequence information to design nucleic acid probes that can be used for isolation, identification, and characterization of lysomal protein genes.

CLN2 has been identified and the translation product of this gene is a novel protease, which when absent or defective results in LINCL. Identification of CLN2 will not only aid in the prevention of LINCL through genetic counseling but will also provide strategies and test systems for therapeutic intervention. In addition, further characterization of this previously unknown lysosomal enzyme may provide useful insights into other more common human neurodegenerative disorders. Furthermore, the utility of a general approach for determining the molecular bases for lysosomal disorders of unknown etiology has been demonstrated (22).

The present invention is broadly directed to an isolated and characterized LINCL-associated gene (CLN2) and gene product (CLN2). CLN2 is a pepstatin-insensitive carboxyl protease. In a specific embodiment, CLN2 has an amino acid sequence as depicted in FIG. 3 (SEQ ID NO:3). In another specific embodiment, CLN2 has a nucleotide sequence as depicted in FIG. 3 (SEQ ID NO:1).

CLN2 is expressed in healthy individuals. However, LINCL patients have either no CLN2 or express a defective (mutant) CLN2. Thus, the present invention advantageously provides a materials capable of ameliorating LINCL by delivering wild-type CLN2 to LINCL patients either through gene therapy or a administration of a pharmaceutical preparation of CLN2 or a CLN2 analog.

The present invention further relates to a chimeric protein comprising the protein or fragment thereof. In specific embodiments, infra, such a chimeric protein consists of maltose binding protein or poly-histidine with CLN2. However, the invention specifically contemplates chimeric proteins comprising a targeting moiety, preferably an intracellular targeting moiety, with CLN2.

Naturally, in addition to the isolated protein and fragments thereof, the invention provides a purified nucleic acid encoding a CLN2 protease, or a fragment thereof having at least 15 nucleotides. In a specific embodiment, the nucleic acid encodes CLN2 having an amino acid sequence as depicted in FIG. 3 (SEQ ID NO:3). In a more specific embodiment, the nucleic acid has a nucleotide sequence as depicted in FIG. 3 (SEQ ID NO:1). The invention further provides 5' and 3' non-coding sequences, as depicted in FIG. 3 and SEQ ID NO:1. The invention still further provides an alternatively spliced product (still coding for the same full-length CLN2 protease), as depicted in FIG. 3 and SEQ ID NO:2.

In a specific embodiment, the purified nucleic acid is DNA. The DNA may be provided in a recombinant DNA vector. Preferably, the DNA vector is an expression vector, wherein the DNA encoding the CLN2 is operatively associated with an expression control sequence, whereby transformation of a host cell with the expression vector provides for expression of CLN2, or a fragment thereof as set forth above. Thus, the invention further provides a transformed host cell comprising the DNA vector. In a specific embodiment, the host cell is a bacterial cell. In another specific embodiment, the host cell is a mammalian cell.

The invention further provides a recombinant virus comprising the DNA expression vector. The recombinant virus may be selected from the group consisting of a retrovirus, herpes simplex virus (HSV), papillomavirus, Epstein Barr virus (EBV), adenovirus, and adeno-associated virus (AAV).

Corollary to the recombinant DNA expression vectors, the invention provides a method for producing a CLN2 comprising expressing the expression vector in a recombinant host cell of the invention under conditions that provide for expression of the CLN2 The methods of expression of the invention may be practiced, for example, in a bacterium, or in a mammalian cell.

The nucleic acids of the invention also provide a method for increasing the level of expression of a CLN2 Accordingly, an expression vector may be introduced into a host in vivo under conditions that provide for expression of the CLN2. In one embodiment, the expression vector is a viral expression vector. In another embodiment, the expression vector is a naked DNA expression vector.

The invention further provides a method for treating LINCL by increasing the level of CLN2 in patients with LINCL. In one embodiment, the level of CLN2 is increased by administration of CLN2. In another embodiment, the level of CLN2 is increased by administration of a recombinant expression vector to the cells demonstrating uncontrolled proliferation, which expression vector provides for expression of the CLN2 in vivo. In one embodiment, the expression vector is a viral expression vector; alternatively, the expression vector is a naked DNA expression vector.

The present invention provides a protease assay (specific for CLN2 protease) to determine LINCL prognosis and the efficacy of any therapeutic treatment of the disease.

In addition to therapeutic aspects, the present invention provides oligonucleotides and antibodies for detection of CLN2, and diagnosis of conditions associated with decreased levels of wild-type CLN2 expression.

Thus, in one aspect, the invention provides an oligonucleotide of greater than 20 nucleotides which hybridizes under stringent conditions to the nucleic acid encoding CLN2. Preferably, the oligonucleotide hybridizes under conditions wherein the $T_m$ is greater than 60° C. More preferably, the oligonucleotide hybridizes at a $T_m$ of greater than 65° C. In another embodiment, the oligonucleotide hybridizes at 40% formamide, with 5× or 6×SCC. In a specific embodiment, exemplified infra, the oligonucleotide is an antisense oligonucleotide that hybridizes to CLN2 mRNA.

In another aspect, the invention provides an antibody specific for CLN2 The antibody may be polyclonal or monoclonal. In a specific embodiment, exemplified infra, the antibody is a rabbit polyclonal antibody generated against a CLN2 fusion protein. In a specific embodiment, the antibody is labeled, e.g., with a label selected from the group consisting of a radioisotope, an enzyme, a chelating agent, a fluorophore, a chemiluminescent molecule, and a particle.

The oligonucleotides and antibodies of the invention can be used to detect the presence or level of CLN2, or nucleic acids encoding it, in a biological sample. In one embodiment, the invention provides a method for detecting CLN2 in a biological sample comprising contacting a biological sample with an antibody specific for CLN2 under conditions that allow for antibody binding to antigen; and detecting formation of reaction complexes comprising the antibody and CLN2 in the sample. The detection of formation of reaction complexes indicates the presence of CLN2 in the sample. The level of CLN2 can be quantitated by evaluating the amount of reaction complexes formed, wherein the amount of reaction complexes corresponds to the level of CLN2 in the biological sample. Alternatively, a method for detecting CLN2 mRNA in a biological sample comprises contacting a biological sample with an oligonucleotide of the invention under conditions that allow for hybridization with mRNA; and detecting hybridization of the oligonucleotide to mRNA in the sample. The detection of hybridization indicates the presence of CLN2 mRNA in the sample. The level of expression of CLN2 mRNA can be determined by evaluating the quantity of oligonucleotide hybridized, wherein the quantity of oligonucleotide hybridized corresponds to the level of CLN2 in the biological sample.

Thus, a primary object of the invention is to provide a novel lysosomal protein that is a pepstatin-insensitive carboxyl protease (CLN2), mutants of which, or absence of, is causative of LINCL.

Another object of the invention is to provide a nucleic acid, preferably a DNA molecule, coding for such a protein.

Still another object of the invention is to ameliorate LINCL by administering CLN2-gene therapy or CLN2 protease, and variants thereof, in a pharmaceutical composition.

These and other objects of the present invention will be better understood by reference to the following Drawings and the Detailed Description of the Invention.

BRIEF DESCRIPTION OF THE DRAWINGS

FIG. 3. Nucleotide sequence of the human CLN2 mRNA and conceptual amino acid sequence. The nucleotide sequence shown is a composite derived from the complete sequences of 68 ESTs which together cover nucleotides 21-3487, a human genomic clone encompassing the entire gene except the first 236 nucleotides and two independent PCR products from a human cortex cDNA library which encoded the most 5' 146 nucleotides including the probable initiation codon. An unfilled arrow indicates the predicted signal cleavage site and a filled arrow indicates the known N-terminus of the mature/heavy chain. Potential N-linked glycosylation sites are indicated by heavy underlining and the boxed region indicates the N-terminal amino acid sequence obtained from the purified protein. * indicates amino acids which are mutated in LINCL patients. Dashed underlining indicates a likely polyA addition consensus sequence for the longer transcript and the position of the polyA tail of the shorter transcript is also indicated. Note: there appears to be a polymorphism in the 3' UTS (S at 2824); of 20 EST sequences examined, 13 were G at this position and 7 were C.

FIG. 4. Sequence similarities to CLN2. Aligned sequences of the human CLN2 protein, *Pseudomonas* sp. 101 pepstatin-insensitive carboxyl proteinase (PsCP), and *Xanthomonas* sp. T-22 pepstatin-insensitive carboxyl proteinase (XaCP). Shading indicates regions of amino acid conservation: heavy shading indicates identical amino acids and light shading indicates similar amino acids. Predicted and known peptide cleavage sites are indicated by unfilled and filled arrows, respectively. XaCP has a 192 amino acid C-terminal extension (ellipsis) that is proteolytically removed.

FIG. 5. Enzymatic activity of CLN2. Pepstatin sensitive and insensitive protease activities in extracts of normal and LINCL brain samples. Samples were homogenized in 50 volumes (w/v) of 0.15 M NaCl. 0.1% Triton X-100 and centrifuged at 14,000×g for 25 min. Pepstatin insensitive activity in the supernatant was measured using 1% bovine hemoglobin as a substrate in 25 mM formate buffer containing 2 μM pepstatin, 0.1 mM E-64, 0.15 M NaCl and 0.1% Triton X-100 pH 3.5. The TCA soluble degradation products were quantitated with fluorescamine (S. De Bernardo, et al., *Archives of Biochemistry and Biophysics* 163, 390-399 (1974)) in borate buffer pH 8.6. Cathepsin D activity was measured under identical conditions but omitting pepstatin.

DETAILED DESCRIPTION OF THE INVENTION

Figure 1:
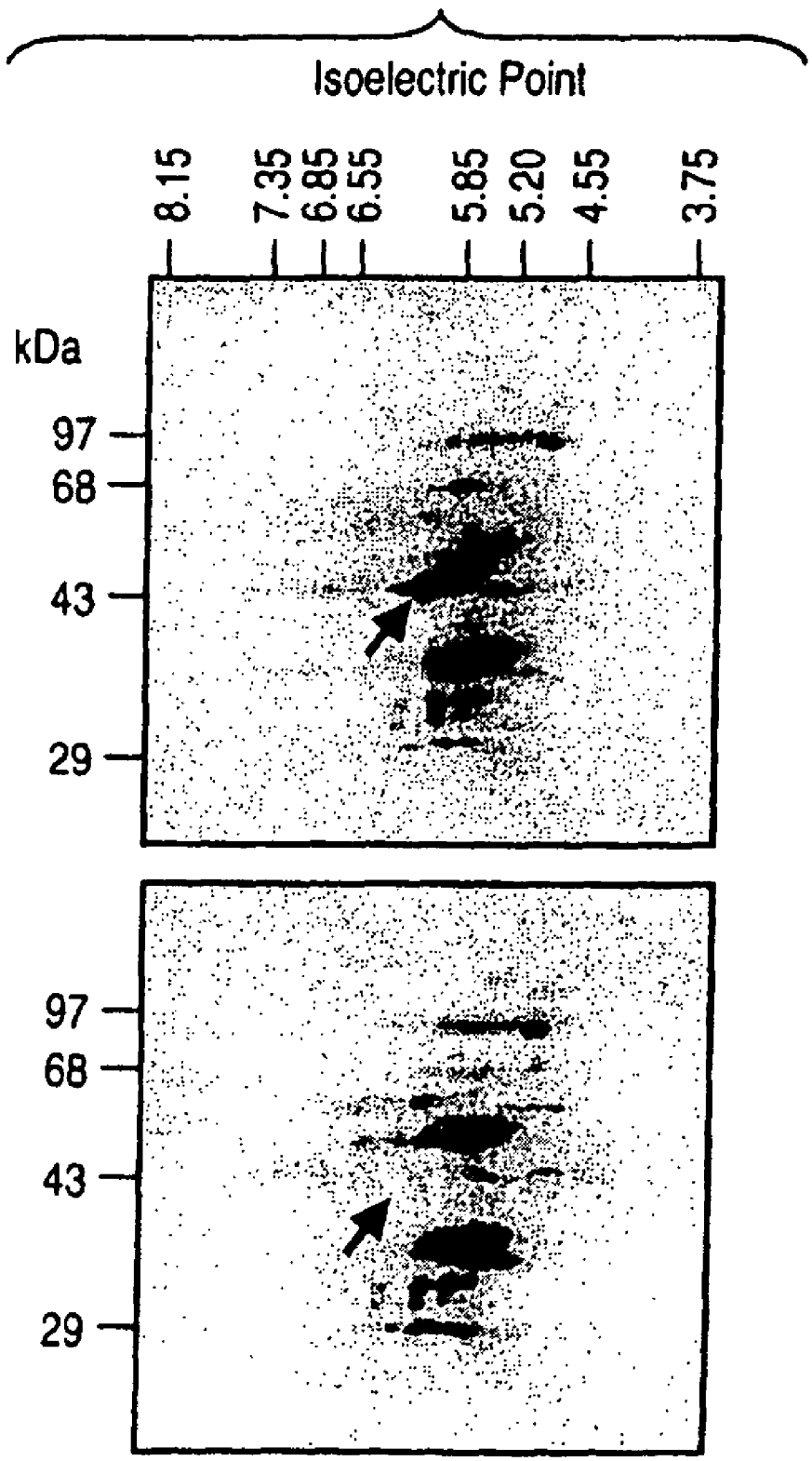
FIG. 1. A protein deficient in LINCL. Detergent solubilized extracts of gray matter (50 μg protein) from normal (top) or LINCL (bottom) brain autopsy specimens were fractionated by isoelectric focusing and SDS-PAGE, transferred to nitrocellulose, and Man 6-P glycoproteins detected using $^{125}$I-labeled MPR. The Man 6-P glycoprotein that is absent in LINCL extracts is arrowed.

The invention provides a novel pepstatin-insensitive carboxyl protease, termed herein CLN2, including biologically active fragments thereof.

For purposes of the present description, the term "isolated" means at the least removed from a natural cellular location. Preferably, CLN2 is purified, so that it comprises at least 50%, preferably at least 75%, and more preferably at least 90% of protein (in the case of a nucleic acid, of nucleic acids) in a sample.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

In a specific embodiment, the term about means within about 20%, preferably within about 10%, and more preferably within about 5%, of the value modified.

The term "CLN2" (note absence of italics) is interchangeable with "CLN2 protein", "CLN2 protease", and "CLN2 pepstatin-insensitive carboxyl protease". CLN2 has the amino acid sequence depicted in FIG. 3 and in SEQ ID NO:3.

The term "*CLN2*" (note presence of italics) is used in reference to the gene and the mRNA encoding the CLN2 protease. *CLN2* has the amino acid sequence depicted in FIG. 3 and in SEQ ID NO:2. Additionally, an alternatively spliced form of the mRNA is depicted in FIG. 3 and in SEQ ID NO: 2.

The term "LINCL" is an acronym for classical late infantile neuronal ceroid lipofuscinosis.

In addition to the CLN2 protein and polypeptide fragments, the invention contemplates chimeric proteins with CLN2 or a fragment thereof. A CLN2 fusion protein comprises at least a functionally active portion of a non-CLN2 protein (termed herein the "fusion partner") joined via a peptide bond to at least a functionally active portion of a CLN2 polypeptide. The non-CLN2 sequences can be amino- or carboxyl-terminal to the CLN2 sequences. In specific embodiments, infra, CLN2 and the catalytic domain polypeptide fragment of CLN2 are expressed as fusion proteins, in which the fusion partner is maltose binding protein or polyhistidine. However, the present invention contemplates fusion to any protein (or polypeptide), including marker proteins such as lacZ, signal peptides for extracellular or periplasmic expression, and different nuclear localization peptides, to mention but a few possibilities. The invention further contemplates joining CLN2, or a polypeptide fragment domain thereof, with a different protein to create a hybrid fusion protein having different target specificity, particularly targeting for intracellular translocation, catalytic activity, or other combinations of properties from the CLN2 or fragment of the invention with the fusion partner. A recombinant DNA molecule encoding such a fusion protein comprises a sequence encoding at least a functionally active portion of a non-CLN2 protein joined in-frame to the CLN2 coding sequence, and preferably encodes a cleavage site for a specific protease, e.g., thrombin or Factor Xa, preferably at the CLN2- non-CLN2 juncture. In a specific embodiment, the fusion protein is expressed in *Escherichia coli*.

Genes Encoding CLN2 Protease

The present invention contemplates isolation of a gene encoding a CLN2 protein of the invention, including a full length, or naturally occurring form of CLN2, and any antigenic fragments thereof from any animal, particularly mammalian or avian, and more particularly human, source. As used herein, the term "gene" refers to an assembly of nucleotides that encode a polypeptide, and includes cDNA and genomic DNA nucleic acids.

Thus, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); Oligonucleotide Synthesis (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication, i.e., capable of replication under its own control.

A cell has been "transfected" by exogenous or heterologous DNA when such DNA has been introduced inside the cell. A cell has been "transformed" by exogenous or heterologous DNA when the transfected DNA expresses mRNA, which preferably is translated into a protein. Usually, expression of such a protein effects a phenotypic or functional change in the cell. However, the protein may be expressed without significantly effecting the cell, e.g., in the instance of fermentation of transformed cells for production of a recombinant polypeptide. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA, and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g. 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA. DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid is at least about 10 nucleotides; more preferably at least about 15 nucleotides; most preferably the length is at least about 20 nucleotides.

In a specific embodiment, the term "standard hybridization conditions" refers to a $T_m$ of 55° C. and utilizes conditions as set forth above. In a preferred embodiment, the $T_m$ is 60° C.; in a more preferred embodiment, the $T_m$ is 65° C.

As used herein, the term "oligonucleotide" refers to a nucleic acid, generally of at least 18 nucleotides, that is hybridizable to a genomic DNA molecule, a cDNA molecule, or an mRNA molecule encoding CLN2 Oligonucleotides can be labeled, e.g., with $^{32}$P-nucleotides or nucleotides to which a label, such as biotin, has been covalently conjugated (see the discussion, supra, with respect to labeling polypeptides). In one embodiment, a labeled oligonucleotide can be used as a probe to detect the presence of a nucleic acid encoding CLN2. In another embodiment, oligonucleotides (one or both of which may be labeled) can be used as PCR primers, either for cloning full length or a fragment of CLN2, or to detect the presence of nucleic acids encoding CLN2 In a further embodiment, an oligonucleotide of the invention can form a triple helix with a CLN2 DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to prokaryotic sequences, cDNA from eukaryotic mRNA, genomic DNA sequences from eukaryotic (e.g. mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control of", "operably associated with", or "operatively associated with" transcriptional and translational (i.e. expression) control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667).

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g. Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group. Program Manual for the GCG Package. Version 7. Madison, Wis.) pileup program.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

A gene encoding CLN2, whether genomic DNA or cDNA, can be isolated from any source, particularly from a human cDNA or genomic library. Methods for obtaining the CLN2 gene are well known in the art, as described above (see, e.g., Sambrook et al., 1989, supra).

Accordingly, any animal cell potentially can serve as the nucleic acid source for the molecular cloning of a CLN2 gene. The DNA may be obtained by standard procedures known in the art from cloned DNA (e.g., a DNA "library"), and preferably is obtained from a cDNA library prepared from tissues with high level expression of the protein, by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA. DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired CLN2 gene may be accomplished in a number of ways. For example, if an amount of a portion of a CLN2 gene or its specific RNA, or a fragment thereof, is available and can be purified and labeled, the generated DNA fragments may be screened by nucleic acid hybridization to the labeled probe (Benton and Davis, 1977, *Science* 196:180; Grunstein and Hogness, 1975, *Proc. Natl. Acad. Sci. U.S.A.* 72:3961). For example, a set of oligonucleotides corresponding to the cDNA for the CLN2 protein can be prepared and used as probes for DNA encoding CLN2, as was done in a specific example, infra, or as primers for cDNA or mRNA (e.g., in combination with a poly-T primer for RT-PCR). Preferably, a fragment is selected that is highly unique to CLN2 of the invention. Those DNA fragments with substantial sequence similarity to the probe will hybridize. As noted above, the greater the degree of sequence similarity, the more stringent hybridization conditions can be used. In a specific embodiment, low stringency hybridization conditions (50° C., 50% formamide, 5×SSC, 5×Denhardts solution) can be used to identify a homologous CLN2 gene, preferably a human CLN2 gene, using a murine CLN2 cDNA probe.

Further selection can be carried out on the basis of the properties of the gene, e.g., if the gene encodes a protein product having the isoelectric, electrophoretic, amino acid composition, uniquely characteristic set of structural domains, or partial amino acid sequence of CLN2 protein as disclosed herein. Thus, the presence of the gene may be detected by assays based on the physical, chemical, or immunological properties of its expressed product. For example, the rabbit polyclonal antibody to murine or human CLN2, described in detail infra, may be used to confirm expression of CLN2. In another aspect, a protein that has an apparent molecular weight of 46 kDa, and which is biochemically determined to have a pepstatin-insensitive carboxyl protease activity, is a good candidate for CLN2.

A preferred embodiment of the invention comprises a novel method for identifying genes which encode lysosomal proteins. This method relies on the observation that all lysosomal enzymes are glycosylated with mannose 6-phosphate (Man 6-P). Therefore, these proteins can be readily purified using an affinity chromatography matrix comprised of the mannose 6-phosphate receptor (MPR) (which also has functionality, in the form of enzyme- or radio-labeled conjugates, for visualization in blotting applications) immobilized on a solid support. Proteins purified on this affinity matrix can be sequenced and thus yield the critical information for designing nucleic acid probes for use in isolation and identification of the gene.

The present invention also relates to cloning vectors containing genes encoding CLN2, active fragments thereof, analogs, and derivatives of CLN2 of the invention, that have the same or homologous functional activity as CLN2, and homologs thereof from other species. The production and use of derivatives and analogs related to CLN2 are within the scope of the present invention. For example, a fragment corresponding to the catalytic domain exhibits enzymatic activity. In a specific embodiment, the derivative or analog is functionally active, i.e., capable of exhibiting one or more functional activities associated with a full-length, wild-type CLN2 of the invention.

CLN2 derivatives can be made by altering encoding nucleic acid sequences by substitutions, additions or deletions that provide for functionally equivalent molecules. Preferably, derivatives are made that have enhanced or increased functional activity relative to native CLN2

Due to the degeneracy of nucleotide coding sequences, other DNA sequences which encode substantially the same amino acid sequence as a CLN2 gene may be used in the practice of the present invention. These include but are not limited to allelic genes, homologous genes from other species, and nucleotide sequences comprising all or portions of CLN2 genes which are altered by the substitution of different codons that encode the same amino acid residue within the sequence, thus producing a silent change. Likewise, the CLN2 derivatives of the invention include, but are not limited to, those containing, as a primary amino acid sequence, all or part of the amino acid sequence of a CLN2 protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Substitutions of glu for asp and visa versa, or "switching" acid amino acid residues with other residues, while retaining the total number of acidic residues in the acidic domain, are expected to retain the functional activity of that domain.

Amino acid substitutions may also be introduced to substitute an amino acid with a particularly preferable property. For example, a Cys may be introduced a potential site for disulfide bridges with another Cys. A His may be introduced as a particularly "catalytic" site (i.e. His can act as an acid or base and is the most common amino acid in biochemical catalysis). Pro may be introduced because of its particularly planar structure, which induces β-turns in the protein's structure.

The genes encoding CLN2 derivatives and analogs of the invention can be produced by various methods known in the art. The manipulations which result in their production can occur at the gene or protein level. For example, the cloned CLN2 gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of CLN2, care should be taken to ensure that the modified gene remains within the same translational reading frame as the CLN2 gene, uninterrupted by translational stop signals, in the gene region where the desired activity is encoded.

Additionally, the CLN2-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated CLN2 gene product. Any technique for mutagenesis known in the art can be used, including but not limited to in vitro site-directed mutagenesis (Hutchinson, C. et al., 1978. *J. Biol. Chem.* 253:6551; Zoller and Smith, 1984, *DNA* 3:479-488: Oliphant et al., 1986, *Gene* 44:177: Hutchinson et al., 1986, *Proc. Natl. Acad. Sci. U.S.A.* 83:710), use of TAB linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pMal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2µ plasmid.

The present invention extends to the preparation of antisense nucleotides, including ribozymes, that may be used to detect the presence of mRNA coding for CLN2 or interfere with the expression of CLN2 at the translational level. This approach utilizes antisense nucleic acid and ribozymes to hybridize to CLN2 mRNA, which can block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule (see Marcus-Sekura, 1988, *Anal. Biochem.* 172:298). In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro (Marcus-Sekura, 1988, supra; Hambor et al., 1988, *J. Exp. Med.* 168:1237). Preferably synthetic antisense nucleotides contain phosphoester analogs, such as phosphorothioates, or thioesters, rather than natural phosphoester bonds. Such phosphoester bond analogs are more resistant to degradation, increasing the stability, and therefore the efficacy, of the antisense nucleic acids.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech. 1988, *J. Am. Med. Assoc.* 260:3030). Because they are sequence-specific, only mRNAs with particular sequences are inactivated.

Investigators have identified two types of ribozymes, *Tetrahymena*-type and "hammerhead"-type (Hasselhoff and Gerlach, 1988). *Tetrahymena*-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to *Tetrahymena*-type ribozymes for inactivating a specific mRNA species, and eighteen base recognition sequences are preferable to shorter recognition sequences.

The DNA sequences encoding CLN2, and variants (e.g. mutants associated with LINCL) thereof, described and enabled herein may thus be used to prepare antisense molecules that hybridize to and ribozymes that cleave mRNAs for CLN2, thus inhibiting expression of the gene encoding CLN2. A preferred embodiment would entail targeting mutant alleles of the CLN2 gene associated with LINCL.

Expression of CLN2 Proteins

The nucleotide sequence coding for CLN2, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding CLN2 of the invention is operably associated with a promoter in an expression vector of the invention. Both cDNA and genomic sequences can be cloned and expressed under control of such regulatory sequences. An expression vector also preferably includes a replication origin, unless the vector is intended for homologous recombination.

The necessary transcriptional and translational signals can be provided on a recombinant expression vector, or they may be supplied by the native gene encoding CLN2 and/or its flanking regions.

As pointed out above, potential chimeric partners for CLN2 include substitute catalytic domains, or a different nuclear targeting domain.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant CLN2 protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding CLN2 is cultured in an appropriate cell culture medium under conditions that provide for expression of CLN2 by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of CLN2 protein may be controlled by any promoter/enhancer element known in the art, but these regulatory elements must be functional in the host selected for expression. Promoters which may be used to control CLN2 gene expression include, but are not limited to, the SV40 early promoter region (Benoist and Chambon, 1981, *Nature* 290: 304-310), the promoter contained in the 3' long terminal repeat of Rous sarcoma virus (Yamamoto, et al., 1980, *Cell* 22:787-797), the herpes thymidine kinase promoter (Wagner et al., 1981, *Proc. Natl. Acad. Sci. U.S.A.* 78:1441-1445), the regulatory sequences of the metallothionein gene (Brinster et al., 1982, *Nature* 296:39-42); prokaryotic expression vectors such as the β-lactamase promoter (Villa-Kamaroff, et al., 1978, *Proc. Natl. Acad. Sci. U.S.A.* 75:3727-3731), or the tac promoter (DeBoer, et al., 1983, *Proc. Natl. Acad. Sci. U.S.A.* 80:21-25); see also "Useful proteins from recombinant bacteria" in Scientific American, 1980, 242:74-94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); insulin gene control region which is active in pancreatic beta cells (Hanahan, 1985, *Nature* 315:115-122), immunoglobulin gene control region which is active in lymphoid cells (Grosschedl et al., 1984, *Cell* 38:647-658; Adames et al., 1985, *Nature* 318: 533-538; Alexander et al., 1987, *Mol. Cell. Biol.* 7:1436-1444), mouse mammary tumor virus control region which is active in testicular, breast, lymphoid and mast cells (Leder et al., 1986, *Cell* 45:485-495), albumin gene control region which is active in liver (Pinkert et al., 1987, *Genes and Devel.* 1:268-276), alpha-fetoprotein gene control region which is active in liver (Krumlauf et al., 1985, *Mol. Cell. Biol.* 5:1639-1648; Hammer et al., 1987, *Science* 235:53-58), alpha 1-antitrypsin gene control region which is active in the liver (Kelsey et al., 1987, *Genes and Devel.* 1:161-171), beta-globin gene control region which is active in myeloid cells (Mogram et al., 1985, *Nature* 315:338-340; Kollias et al., 1986, *Cell* 46:89-94), myelin basic protein gene control region which is active in oligodendrocyte cells in the brain (Readhead et al., 1987, *Cell* 48:703-712), myosin light chain-2 gene, control region which is active in skeletal muscle (Sani, 1985, *Nature* 314:283-286), and gonadotropic releasing hormone gene control region which is active in the hypothalamus (Mason et al., 1986, *Science* 234:1372-1378).

Expression vectors containing a nucleic acid encoding a CLN2 of the invention can be identified by four general approaches: (a) PCR amplification of the desired plasmid DNA or specific mRNA, (b) nucleic acid hybridization, (c) presence or absence of selection marker gene functions, (d) analysis with appropriate restriction endonucleases, and (e) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g. β-galactosidase activity, thymidine kinase activity, resistance to antibiotics, transformation phenotype, occlusion body formation in baculovirus, etc.) caused by the insertion of foreign genes in the vector. In another example, if the nucleic acid encoding CLN2 is inserted within the "selection marker" gene sequence of the vector, recombinants containing the CLN2 insert can be identified by the absence of the CLN2 gene function. In the fourth approach, recombinant expression vectors can be identified by digestion with appropriate restriction enzymes, followed by molecular weight analysis of resulting digestion products (fragments). In the fifth approach, recombinant expression vectors can be identified by assaying for the functional, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMal-C2, pET, pGEX (Smith et al, 1988, *Gene* 67:31-40), pMB9 and their derivatives, plasmids such as RP4; phage DNAS, e.g., the numerous derivatives of phage λ, e.g., NM989, and other phage DNA, e.g., M13 and filamentous single stranded phage DNA: yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to p VL941 (BamH1 cloning site; Summers), pVL1393 (BamH1, SmaI, XbaI, EcoRI, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlue BacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen (195)), and pBlueBacHisA, B, C (three different reading frames, with BamH1, BglII, PstI, NcoI, and HindIII cloning site, an N-terminal peptide for ProBond purification, and blue/white recombinant screening of plaques: Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, Current Protocols in Molecular Biology, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible metallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI. XbaI cloning site. G418 selection; Invitrogen), and others. Vaccinia virus mammalian expression vectors (see, Kaufman, 1991, supra) for use according to the invention include but are not limited to pSC11 (SmaI cloning site. TK- and β-gal selection), pMJ601 (SalI, SmaI, AflI, NarI, BspMII. BamHI, ApaI, NheI, SacII, KpnI, and HindIII cloning site: TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express OB polypeptide. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., (lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g. glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. Expression in yeast can produce a glycosylated product. Expression in eukaryotic cells can increase the likelihood of "native" folding of a heterologous protein. Moreover, expression in mammalian cells can provide a tool for reconstituting, or constituting, CLN2 activity. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun (biolistics), or a DNA vector transporter (see, e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990).

Antibodies to CLN2

According to the invention, CLN2 protein purified from natural sources, produced recombinantly or by chemical synthesis, and fragments or other derivatives or analogs thereof, including fusion proteins, may be used as an immunogen to generate antibodies that recognize the CLN2 protein or mutant variants associated with LINCL. Such antibodies are referred to a specific for CLN2, or characterized by specific binding to CLN2. Such antibodies include but are not limited to polyclonal, monoclonal, chimeric, single chain, Fab fragments, and an Fab expression library. In specific embodiments, infra, a CLN2-poly-histidine fusion protein, and a CLN2-maltose binding protein (MBP) fusion protein were used as antigens. The anti-CLN2 antibodies of the invention may be cross reactive, e.g., they may recognize CLN2 from different species. Polyclonal antibodies have greater likelihood of cross reactivity. Alternatively, an antibody of the invention may be specific for a single form of CLN2, such as murine CLN2. Preferably, such an antibody is specific for human CLN2.

Various procedures known in the art may be used for the production of polyclonal antibodies to CLN2 protein a recombinant CLN2 or derivative or analog thereof. For the production of antibody, various host animals can be immunized by injection with the CLN2 protein, or a derivative (e.g., fragment or fusion protein) thereof, including but not limited to rabbits, mice, rats, sheep, goats, etc. In one embodiment, the CLN2 protein, or more preferably a fragment thereof, can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebaaerium parvum*.

For preparation of monoclonal antibodies directed toward the CLN2 protein, or fragment, analog, or derivative thereof, any technique that provides for the production of antibody molecules by continuous cell lines in culture may be used. These include but are not limited to the hybridoma technique originally developed by Kohler and Milstein (1975, *Nature* 256:495-497), as well as the trioma technique, the human B-cell hybridoma technique (Kozbor et al., 1983, *Immunology Today* 4:72), and the EBV-hybridoma technique to produce human monoclonal antibodies (Cole et al., 1985, in *Monoclonal Antibodies and Cancer Therapy*, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1933, *Proc. Natl. Acad. Sci. U.S.A.* 80:2026-2030) or by transforming human B cells with EBV virus in vitro (Cole et al., 1985, in *Monoclonal Antibodies and Cancer Therapy*. Alan R. Liss. pp. 77-96). In fact, according to the invention, techniques developed for the production of "chimeric antibodies" (Morrison et al., 1984, *J. Bacteriol.* 159-870: Neuberger et al., 1934, *Nature* 312:604-608; Takeda et al., 1985, *Nature* 314.452-454) by splicing the genes from a mouse antibody molecule specific for a CLN2 protein together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. No. 4,946,778) can be adapted to produce CLN2 protein-specific single chain antibodies. An additional embodiment of the invention utilizes the techniques described for the construction of Fab expression libraries (Huse et al., 1989, *Science* 246:1275-1281) to allow rapid and easy identification of monoclonal Fab fragments with the desired specificity for a CLN2 protein, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., eel agglutination assays, hemagglutination assays), complement fixation assays, immunofluorescence assays, protein A assays. Immunoelectrophoresis assays, or enzymatic assay for CLN2, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a CLN2 protein, one may assay generated hybridomas for a product which binds to a CLN2 protein fragment containing such epitope. For selection of an antibody specific to a CLN2 protein from a particular species of animal, one can select on the basis of positive binding with CLN2 protein expressed by or isolated from cells of that species of animal.

According to the invention, the antibodies specific for CLN2 can be labeled. Suitable labels include enzymes, fluorophores (e.g. fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Cl$, $^{51}Cr$, $^{57}Co$, $^{57}Co$, $^{59}Fe$, $^{90}Y$, $^{125}I$, $^{131}I$ and $^{186}Re$ are used, known currently available counting procedures may be utilized. In the instance where the label is an enzyme, detection may be accomplished by any of the presently utilized colorimetric, spectrophotometry, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g., U.V. light to promote fluorescence. Among examples of colored labels, which can be used according to the present invention, include metallic sol particles, for example, gold sol particles such as those described by Leuvering (U.S. Pat. No. 4,313,734); dye sole panicles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70, 419-439, 1980 and in U.S. Pat. No. 4,857,453.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as [$^{35}S$]-methionine or [$^{32}$]-orthophosphate. In addition to metabolic (or biosynthetic) labeling with [$^{35}S$]-methionine, the invention further contemplates labeling with [$^{14}C$]-amino acids and [$^{3}H$]-amino acids (with the tritium substituted at non-labile positions).

The foregoing antibodies can be used in methods known in the art relating to the localization and activity of the CLN2 protein, e.g., for Western blotting, imaging CLN2 protein in situ, measuring levels thereof in appropriate physiological samples, immunohistochemistry, etc.

In a specific embodiment, antibodies that agonize or antagonize the activity of CLN2 protein, mutant variant associated with LINCL, can be generated.

Detection of CLN2 and Implications Thereof

According to the invention, the presence, amount, or activity level of CLN2 may be a useful prognostic for LINCL and useful tool for assessing the efficacy of LINCL therapeutic treatment. Accordingly, the present invention provides for assays detecting the presence, measuring the amount, and/or quantitating the activity of CLN2 protein or, in the former two cases, mRNA in sample. The diagnostic methods can be used to detect a CLN2 gene or mRNA, or CLN2 protein, in a biological sample from an individual. The biological sample can be a biological fluid comprising cells, such as but not limited to, blood, interstitial fluid, plural effusions, urine, cerebrospinal fluid, and the like. Preferably, CLN2 is detected in blood, which is readily obtained. Alternatively, CLN2 can be detected from cellular sources, such as, but not limited to, tissue biopsies, brain, adipocytes, testes, heart, and the like. For example, cells can be obtained from an individual by biopsy and lysed. e.g., by freeze-thaw cycling, or treatment with a mild cytolytic detergent such as, but not limited to, TRITON X-100, digitonin. NONIDET P(NP)-40, saponin, and the like, or combinations thereof (see, e.g., International Patent Publication WO 92/08981, published May 29, 1992). In yet another embodiment, samples containing both cells and body fluids can be used (see ibid.).

In another embodiment, a lower level or lack of CLN2 expression in a sample LINCL-affected cell compared to a normal cell may be indicative of the LINCL disease. Thus, the invention contemplates a method for detecting LINCL disease in a sample cell comprising detecting the level of mammalian CLN2 in a cell with the LINCL phenotype, and comparing the level of CLN2 detected with the level in a normal cell, wherein a lower level of CLN2 in the sample cell than in the normal cell indicates LINCL disease. The level of CLN2 can be detected by detecting mRNA or CLN2 protein, the latter by immunoassay or biochemistry, as described infra. This method is not only of diagnostic value, but can be used to assess the efficacy of LINCL therapeutic treatment.

In yet another embodiment, the assay can be based on quantitating CLN2 pepstatin-insensitive carboxyl protease activity. Again, this method is not only of diagnostic value, but can be used to assess the efficacy of LINCL therapeutic treatment.

In still yet another embodiment, a method is contemplated for detecting the CLN2 gene, and mutant variants associated with LINCL, in chromosomal samples comprising of: contacting a chromosomal sample from, for example, amniotic fluid, with oligonucleotides complementary to CLN2 or variant mutant alleles of CLN2, under conditions that allow for hybridization; and, detecting hybridization of the oligonucleotides to the chromosomes in the sample. Such a method would prove invaluable as a prenatal screening test for LINCL.

The present invention includes an assay system which may be prepared in the form of a test kit for the quantitative analysis of the extent of the presence of the CLN2, or to identify drugs or other agents that may mimic or block their activity. The system or test kit may comprise a labeled component, such as an antibody or oligonucleotide specific for CLN2 protein or mRNA, respectively. Preferably, an assay kit of the invention also comprises a positive control reagent, either CLN2 protein or CLN2 mRNA, for confirming assay performance, and, if desired, for quantitation.

In one embodiment, the present invention provides for the detection of expression of CLN2 or mRNA encoding CLN2. For example, an antisense oligonucleotide of the invention can be used in standard Northern hybridization analysis to detect the presence, and in some instances quantitate the level of expression, of CLN2 mRNA. An oligonucleotide of the invention may also be used to detect mutations in the CLN2 mRNA or gene, by high stringency hybridization analysis with a mutant specific probe (or a wild-type specific probe) with detection of hybridization or lack thereof indicating whether the gene is mutated. For example, hybridization of a wild-type specific probe indicates no mutation, and lack of hybridization indicates a mutation. The reverse would be true for a mutation-specific probe. The techniques for preparing labeled oligonucleotides and using them to analyze gene expression or mutations are well known in the art.

Alternatively, oligonucleotides of the invention can be used as PCR primers to amplify CLN2 mRNA (e.g., by reverse transcriptase-PCR), or CLN2 genes. The amplified mRNA can be quantified, or either amplified mRNA or genomic DNA can be analyzed for mutations. Mutations in the amplified DNA can be detected by creation or deletion of restriction fragment length polymorphisms (RFLPs) not found in the native gene or cDNA, hybridization with a mutation specific probe (or lack of hybridization with a wild-type specific probe), as well as by other techniques.

The presence or level of CLN2 protein can be measured using by immunoassay using an antibody of the invention. Various immunoassay techniques are known in the art, e.g., as described in the "Antibody" section above. In a specific embodiment, infra, a rabbit polyclonal antiserum detects CLN2. In an immunoassay, an antibody may be introduced into a biological sample. After the antibody has had an opportunity to react with sites within the sample, the resulting product mass may be examined by known techniques, which may vary, e.g., with the nature of the label attached.

Finally, biochemical or immunochemical/biochemical (e.g., immunoprecipitation) techniques can be used to detect the presence and or level of CLN2. For example, in one embodiment, a cell may be metabolically labeled (as described in the "Antibody" section, supra, and the Examples, infra), the cell lysed and analyzed by PAGE, and the presence of a ~46 kDa band evaluated. Furthermore, the band can be quantitated by densitometry. Alternatives to metabolic labeling include Western analysis, silver staining, Coomassie blue staining, etc. In another embodiment, the presence and level of CLN2 activity can be detected enzymatically, e.g., by testing the catalytic activity of a cellular extract or isolated protein corresponding to CLN2.

Therapeutic Aspects of CLN2

Based on the data developed in the Examples, infra, particularly the observation that absence of CLN2 or presence of a mutated variant of CLN2 is associated with LINCL, CLN2 may be employed as a therapeutic to ameliorate LINCL. Thus, according to the invention, CLN2, or an expression vector encoding CLN2, can be administered to a subject in need of treatment for LINCL in order to agonize CLN2 activity and thus ameliorate LINCL. The methods of administration described herein can be employed to agonize or antagonize CLN2 activity.

Various mechanisms are available for increasing CLN2 activity in cells, e.g., direct administration of a construct (chimeric or via chemical derivitization or crosslinking) of CLN2 with a targeting molecule (e.g., transferrin, a hormone, a growth factor, or a target cell-specific antibody) to a subject in need of treatment, or by gene therapy approaches to increase expression of CLN2 in proliferating cells in situ.

A subject in whom administration of CLN2 is an effective therapeutic regimen for LINCL is preferably a human, but can be any animal. Thus, as can be readily appreciated by one of ordinary skill in the art, the methods and pharmaceutical compositions of the present invention are particularly suited to administration to any animal, particularly a mammal, including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc. i.e., for veterinary medical use.

Preferably, a composition of the invention for treatment of LINCL is provided in a pharmaceutically acceptable carrier or excipient. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans, although a pharmaceutically acceptable carrier of the invention may share the attributes of such an approved carrier without itself having been approved. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. According to the invention, where amelioration of LINCL is sought, a therapeutically effective amount of a pharmaceutical composition of the invention will restore pepstatin-insensitive carboxyl protease activity to levels that ameliorate LINCL. A therapeutically effective amount and treatment regimen can be developed for an individual by an ordinary skilled physician, taking into account the age, sex, size, and physical well being, of the patient; the course and extent of the disease or disorder; previous, concurrent, or subsequent treatment regimens and the potential for drug interactions; all of which parameters are routinely considered by a physician in prescribing administration of a pharmaceutical agent.

The instant invention provides for conjugating targeting molecules to CLN2, DNA vectors (including viruses) encoding CLN2, and carriers (i.e., liposomes) for targeting to a desired cell or tissue, e.g., a rumor. "Targeting molecule" as used herein shall mean a molecule which, when administered in vivo, localizes to desired locations).

In various embodiments, the targeting molecule can be a peptide or protein, antibody, lectin, carbohydrate, or steroid.

In one embodiment, the targeting molecule is a protein or peptide ligand of an internalized receptor on the target cell.

In a specific embodiment, the targeting molecule is a peptide comprising the well known RGD sequence, or variants thereof that bind RGD receptors on the surface of cells such as cancer cells, e.g., human ova that have receptors chat recognize the RGD sequence. Other ligands include, but are not limited to, transferrin, insulin, amylin, and the like. Receptor internalization is preferred to facilitate intracellular delivery of CLN2 protein.

In another embodiment, the targeting molecule is an antibody. Preferably, the targeting molecule is a monoclonal antibody. In one embodiment, to facilitate crosslinking the antibody can be reduced to two heavy and light chain heterodimers, or the F(ab')$_2$ fragment can be reduced, and crosslinked to the CLN2 via the reduced sulfhydryl.

Antibodies for use as targeting molecule are specific for cell surface antigen. In one embodiment, the antigen is a receptor. For example, an antibody specific for a receptor on cancer cells, such as melanoma cells, can be used.

This invention further provides for the use of other targeting molecules, such as lectins, carbohydrates, proteins and steroids.

Administration of Targeted CLN2

According to the invention, a therapeutic composition comprising delivery of the invention may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration.

In another embodiment, the therapeutic compound can be delivered in a vesicle, in particular a liposome (see Langer, *Science* 249:1527-1533 (1990); Treat et al., in *Liposomes in the Therapy of Infectious Disease and Cancer*, Lopez-Berestein and Fidler (eds.). Liss, New York, pp. 353-365 (1989); Lopez-Berestein, ibid., pp. 317-327; see generally ibid). To reduce its systemic side effects and increase cellular penetration, this may be a preferred method for introducing CLN2.

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.* 23:61 (1983); see also Levy et al., Science 228: 190 (1985); During et al., *Ann. Neurol.* 25:351 (1989); Howard et al., *J. Neurosurg.* 71:105 (1989)). In yet another embodiment, a controlled release system can be placed in proximity of the therapeutic target, thus requiring only a fraction of the systemic dose (see, e.g., Goodson, in Medical Applications of Controlled Release, supra, vol. 2, pp. 115-138 (1984)). Preferably, a controlled release device is introduced into a subject in proximity of the site LINCL-affected tissue.

Other controlled release systems are discussed in the review by Langer (Science 249:1527-1533 (1990)).

Gene Therapy

In one embodiment, a gene encoding an CLN2 protein or polypeptide domain fragment thereof is introduced in vivo or ex vivo in a nucleic acid vector.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques 7:980-990 (1992)). DNA vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, tumor tissue can be specifically targeted. Examples of particular vectors include, but are not limited to, a defective herpes virus 1 (HSV1) vector (Kaplitt et al., 1991, Molec. Cell. Neurosci. 2:320-330), an attenuated adenovirus vector, such as the vector described by Stratford-Perricaudet et al. (1992, J. Clin. Invest. 90:626-630), and a defective adeno-associated virus vector (Samulski et al., 1987, J. Virol. 61:3096-3101; Samulski et al., 1989, J. Virol. 63:3822-3828).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (see, e.g., Wilson, Nature Medicine (1995)). In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764: Temin et al., U.S. Pat. No. 4,980,289; Markowitz et al., 1988, J. Virol. 62:1120; Temin et al., U.S. Pat. No. 5,124,263; International Patent Publication No. WO 95/07358, published Mar. 16, 1995, by Dougherty et al.; and Kuo et al., 1993, Blood 82:845.

Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner, et. al., 1987, Proc. Natl. Acad. Sci. U.S.A. 84:7413-7417; see Mackey, et al., 1988, Proc. Natl. Acad. Sci. U.S.A. 85:8027-8031)). The use of cationic lipids may promote encapsulation of negatively charged nucleic acids, and also promote fusion with negatively charged cell membranes (Felgner and Ringold, 1989, Science 337:387-388). The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting (see Mackey, et. al., 1988, supra). Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, biolistics (use of a gene gun), or use of a DNA vector transporter (see, e.g., Wu et al., 1992, J. Biol. Chem. 267:963-967; Wu and Wu, 1988, J. Biol. Chem. 263.14621-14624; Hartmut et al., Canadian Patent Application No. 2,012,311, filed Mar. 15, 1990).

The present invention may be better understood by reference to the following Examples, which are provided by way of exemplification and are in no way limiting.

Example 1

Isolation and identification of CLN2 and its corresponding gene product. Since LINCL results from the absence or deficiency of a lysosomal enzyme, then its corresponding Man 6-phosphorylated form should also be absent or decreased. To test this possibility, detergent soluble extracts of autopsy brain samples from a LINCL patient and a normal control were fractionated by 2D gel electrophoresis and Man 6-P glycoproteins detected after transfer to nitrocellulose using an iodinated fragment of the MPR (9) (FIG. 1). Normal brain contains ~75 distinct spots representing multiple isoforms of different Man 6-P containing glycoproteins (FIG. 1, top). LINCL brain is remarkably similar, except one prominent spot is absent (FIG. 1, bottom). The corresponding normal spot has an apparent MW of 46,000 Da and an isoelectric point centered at pH ~6.0. Extracts from 4 LINCL patients were also compared with 3 normal controls by one dimensional SDS-PAGE, with the consistent observation that this major Man 6-phosphorylated glycoprotein in the healthy extracts was absent in the LINCL brain (data not shown).

In order to identify this potential candidate for CLN2, total Man 6-P containing glycoproteins were purified (10, 11) from normal brain by affinity chromatography on a column of immobilized MPR and, after fractionation by SDS-PAGE and transfer to a PVDF membrane, the band that was absent in the LINCL specimens was isolated and sequenced. This sequence was compared against the SWISSPROT database and against the predicted translation products from the GENBANK database using BLASTP and tBLASTN, respectively. No significant sequence homologies were observed, revealing it to be a novel Man 6-P glycoprotein, and thus presumably a previously uncharacterized human lysosomal enzyme. The N-terminal sequence was then compared with predicted translation products from the expressed sequence tag (EST) database (dbEST) using tBLASTN. The initial search of the database detected a murine clone encoding a sequence identical to the peptide in 16 of 20 positions and later releases of dbEST contained human clones identical to the peptide in 19 of 20 positions. By iterative database searching and sequencing select clones[1], a nearly full length sequence for the human CLN2 candidate was assembled (FIG. 3). The 5' end of the human cDNA was obtained by two rounds of polymerase chain amplification of the CLN2 candidate from a human cortex cDNA library (Stratagene) using two different gene specific primers and a single vector-specific primer[2]. The composite sequence of the CLN2 candidate (FIG. 3) was subsequently confirmed from a genomic clone and amplified segments of genomic DNA from LINCL patients and normal controls.

[1] EST cDNA clones mr92b09 (murine) and zo55e03, EST37588 and zo35g10 (human) were sequenced in their entirety. Human EST cDNA clones zs52e09 and zr50co6 were partially sequenced and appear to contain cloning artifacts.
[2] The first round of PCR used the T3 promoter primer with either gene specific primer NR1 (5'-GTGATCACAGAATGGCACTT) or NR2 (5'-AA-CATGGGTTTCCGTAGGTC). The second round of PCR using the products from the first amplification used the T3 promoter primer and NR4 (5'-CTTC-CTCAGGGTCCGCACGG).

Example 2

Figure 2:
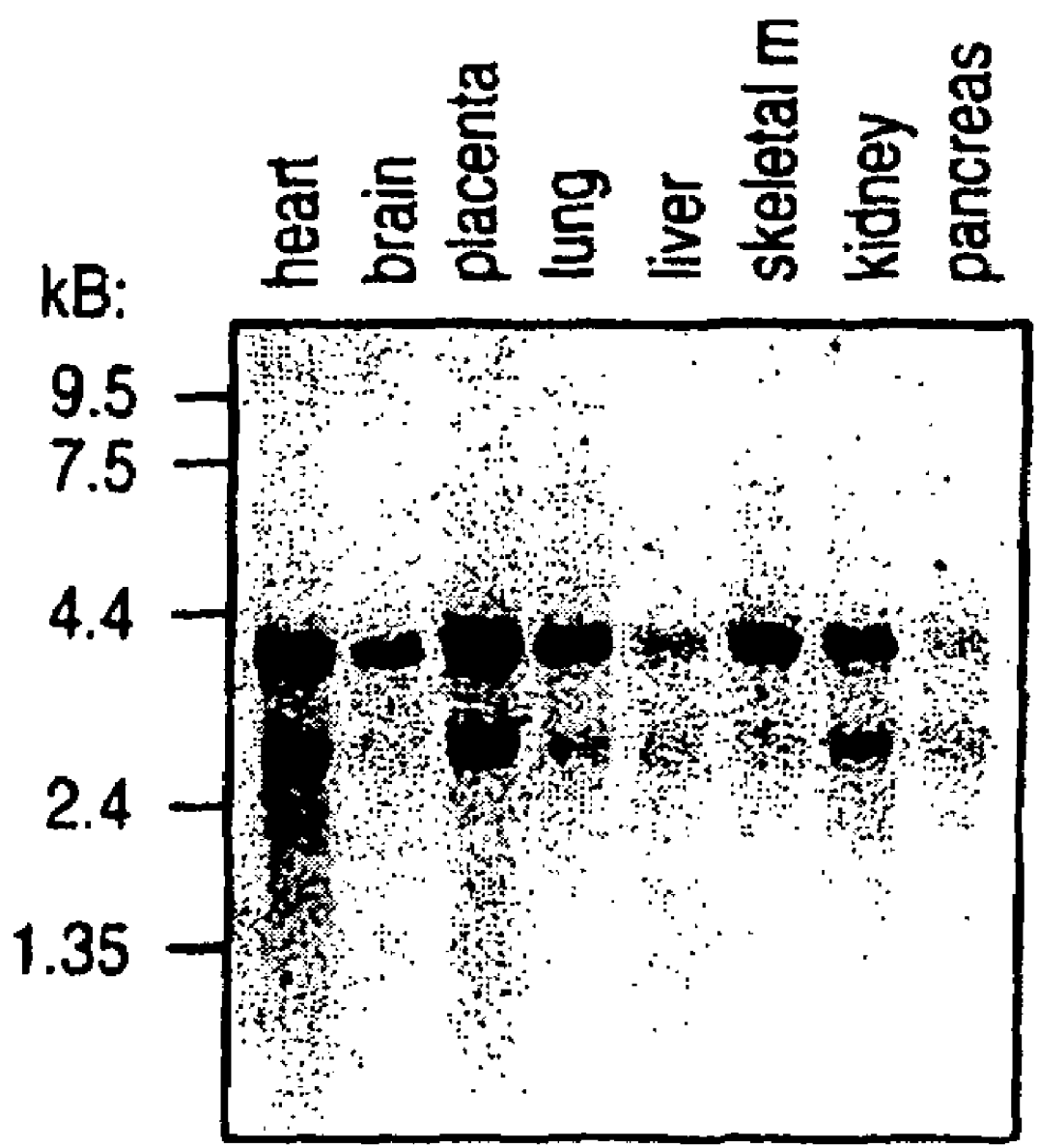
FIG. 2. CLN2 expression in different human tissues. A Northern blot of polyA+ human RNA (CLONTECH, Palo Alto, Calif.) containing 2 μg polyadenylated RNA was probed with the $^{32}$P-labeled insert of EST37588. Hybridization with two transcripts of approximate size 2.7 and 3.7 kb is evident in all tissues. S. muscle; skeletal muscle.

Characterization of CLN2 and its corresponding gene product. The location of polyA tracts on different human EST cDNA clones indicates that there are two transcripts, with the polyA tail starting after nt 2503 for the short transcript and nt 3487 for the long transcript. (FIG. 3). This is confirmed by northern blot analysis, which reveals two transcripts of ~2700 and 3700 nt (FIG. 2). mRNA was detected in all tissues examined (in addition to those tissues shown in FIG. 2, spleen, thymus, prostate, testis, ovary, small intestine, colon and peripheral blood leukocytes also expressed mRNA (not shown)) but levels were highest in heart and placenta and relatively similar in other tissues. The ubiquitous distribution of this mRNA indicated by Northern blotting is confirmed by the existence of highly related clones in many different cDNA libraries as found by database searches.

The CLN2 message long open reading frame encodes a 563-residue protein that is predicted to contain a 16-residue signal sequence (FIG. 3). There are no methionines between the putative initiation codon and the start of the chemically determined sequence at residue 195, indicating that the CLN2 precursor contains a long pro-region or consists of a N-terminal light and a C-terminal heavy chain. As all five potential glycosylation sites reside C-terminal to the cleavage site, should a light chain be present in the mature protein, it would not have been detected using the Man 6-P glycoprotein assay.

The predicted physical properties of the conceptually translated protein are in accordance with the observed properties of the protein that is missing in LINCL brain extracts, which has an apparent MW of 46,000 Da and a pI of 6.0. The calculated MW of the mature protein/heavy chain is 39,700 Da. Assuming all glycosylation sites are utilized and an average MW of 1800 Da for each oligosaccharide, the total MW would be ~48.000 Da. The calculated isoelectric point is 6.13 without considering post-translational modifications e.g., Man 6-P residues, which would shift the isoelectric point towards the acidic range.

The absence of this 46 kDa lysosomal protein in LINCL patients makes it a likely candidate for CLN2. Strong support for this conclusion comes from the observation that the gene identified here maps to chromosome 11p15[3], which is also the locus identified for CLN2 by genetic linkage analysis (3).

[3] Three lines of evidence give corroborative results for an inequivocable localization. 1) There is a nearly perfect match between nt 34-104 of the CLN2 cDNA candidate and Genbank accession number B04497, which represents a PCR amplified fragment of a flow sorted chromosome 11 specific cosmid clone. (The 317 nt B04497 also contains sequence of flanking introns.) 2) There is a perfect 505 nt match between the 3' end of the CLN2 cDNA (nt 2979-3483) and the 5' end (nt 1-505) of Genbank accession number U25816. U25816 consists of 2605 nt that encompass the human TATA-binding protein associated factor II 30 ($TAF_{II}30$) gene. The $TAF_{II}30$ transcription start site is at U25816 nt 1060 and most of the promoter elements are downstream of U25816 nt 860, and thus do not overlap with the 3' end of the large CLN2 candidate transcript. Thus, the CLN2 candidate, gene and the $TAF_{II}30$ gene are physically adjacent. The $TAF_{II}30$ gene was mapped to chromosome 11p15.2-p15.5 using in situ hybridization (E. Scheer, M. G. Mattei, X. Jacq. P. Chambon, L. Tora, *Genomics* 29, 269-72 (1995). 3) Three sequences (accession numbers X72877. X72878, and X72880) representing a cosmid clone have strong matches (p<10^−31) to nt 2817-3264 of the CLN2 candidate cDNA. The cosmid clone maps to chromosome 11p15. Taken together, these results indicate that the CLN2 candidate is localized to chromosome 11p15.

Direct evidence for the identification of CLN2 came from sequence analysis of DNA from LINCL patients and unaffected family members (Table 1). The gene structure (not shown) of the CLN2 candidate was determined by sequence comparison between PCR segments from a genomic clone and the cDNA sequence. This allowed analysis of both intronic and exonic sequences from LINCL patient DNA using genomic DNA prepared from cell lines[4]. Mutations were observed in two of the PCR segments generated from the DNA of LINCL patients. Two unrelated LINCL patients contained mutations within the codon (TGT) encoding Cys 365. In one case, a monoallelic transversion of T to C resulted in a Cys to Arg substitution; presumably the defect in this patient is compound heterozygous and there is therefore an additional as yet unidentified mutant allele. Providing evidence that this substitution represents a deleterious mutation rather than a polymorphism is the observation that another patient contains a different mutation in the same codon. In this case, a homozygous G to A transversion resulted in a Cys to Tyr substitution in the protein expressed from both alleles. Should this Cys prove to be involved in disulfide bonding, mutations are likely to be highly disruptive given the role of disulfide bonds in establishing and maintaining protein structure. Different compound heterozygous mutations were found in two affected siblings. A heterozygous C to T transversion resulted in the conversion of the codon (CGA) for Arg 208 to an umber (TGA) stop codon. In the other allele, the conserved AG of the intronic 3' splice junction sequence is mutated to AC which is likely to result in incorrect splicing of the CLN2 candidate mRNA. Each parent possessed a single different mutant allele and an unaffected sibling possessed only the premature stop mutation, indicating conventional Mendelian inheritance of these mutations. None of these mutations were observed in the genomic clone, placental DNA from a normal subject or in any of the EST sequences which overlap these sites. When considered in conjunction with the chromosomal localization of this protein, the presence of these mutations unequivocally demonstrate that the protein identified here is CLN2.

[4] CLN2 was analyzed in patient DNA extracted from cell lines using overlapping M13 forward/reverse tailed primer pairs. Each pair amplified an exon and flanking intronic sequences and the resulting products were sequenced using dye-labeled −21M13 primer. For patients, the sequence of fragments which mismatched with the consensus sequence was then confirmed by sequencing with the M13 reverse primer. Each fragment containing a mutation in both patients and relatives was then independently reamplified and sequenced on both strands to confirm that the observed heterogeneities were not artifacts of PCR amplification. Primer pairs which detected mutations in patient DNA were SF3(5'TGTAAAACGACGCCCAGTCAGACCTTCCACTAGCGACC)/SRJ(5CAGGAAACAGCTATGACCCTGTAT CCCACACAAGAGAT) and SF0A(5'-TGTAAAACGACGGCCAGTTAGATGCCATTGGGGACTGG)/SR0A(5'-CAGGAAACAGCTATGACCGTCATGGAAATACTGCTCCA). PCR from 1 μg patient DNA using Vent DNA polymerase (New England Biolabs, Beverly, Mass.) was conducted under the following cycle conditions: 94° C. for 3 min followed by 10 cycles of 94° C. for 1 min, 50° C. for 1 min and 72° C. for 1 min, followed by 30 cycles of 94° C. for 1 min. 65° C. for 1 min and 72° C. for 1 min. with a final incubation for 10 min at 72° C. Products were purified using Qiaquick spin columns (Qiagen. Chatsworth, Calif.) and cycle sequenced using AmpliTaq DNA polymerase (Roche Molecular Systems. Inc., Alameda. CA) and ABI Prism dye labeled primers (Perkin Elmer, Foster City, Calif.) on an ABI 373 automated sequencer.

TABLE 1

Genotype Analysis of LINCL Patients.

| cell line* | MUTATION† | | | |
|---|---|---|---|---|
| | splice junction‡ | C636T Arg208Stop | T1107C Cys365Arg | G1108A Cys365Tyr |
| C7786 unaffected sibling | +/+ | −/+ | +/+ | +/+ |

TABLE 1-continued

Genotype Analysis of LINCL Patients.

| | MUTATION† | | | |
|---|---|---|---|---|
| cell line* | splice junction‡ | C636T Arg208Stop | T1107C Cys365Arg | G1108A Cys365Tyr |
| C7787 PROBAND | −/+ | −/+ | +/+ | +/+ |
| C7788 PROBAND | −/+ | −/+ | +/+ | +/+ |
| C7789 mother | +/+ | −/+ | +/+ | +/+ |
| C7790 father | −/+ | +/+ | +/+ | +/+ |
| WG305 | +/+ | +/+ | +/+ | −/− |
| WG308 | +/+ | +/+ | −/+ | +/+ |

†−/+ and −/− represent heterozygous and homozygous mutations, respectively.
*lymphoblasts C7786-C7790 were obtained from the human cell repository at the New York Institute for Basic Research in Developmental Disabilities and are derived from a single family with two LINCL patients; fibroblasts WG305 and WG308 are derived from two unrelated LINCL patients and were obtained from the McGill University Repository for Mutant Human Cell Strains. The parents of patient WG305 were first cousins providing a likely explanation for the homozygosity of the observed mutation.
‡this mutation is a G-C transversion in the genomic sequence immediately preceding T523 of the cDNA sequence.

It is likely that the CLN2 protein represents a previously unidentified type of lysosomal protease. Sequence comparisons revealed significant similarities[5] between the CLN2 candidate with carboxyl peptidases from *Pseudomonas* (13) (PsCP) (17) and *Xanthomonas* (14) (XaCP) (18). Multiple alignments between the CLN2 candidate and the two bacterial proteases reveal significant blocks of sequence similarities and both PsCP and XaCP have long propieces, with mature amino termini located proximal to the known amino terminus of the mature/heavy chain CLN2 candidate (FIG. 4, upper panel). PsCP and XaCP are highly unusual carboxyl proteinases that are not inhibited by pepstatin, the classical inhibitor of pepsin, cathepsin D, and other aspartyl proteases.

[5]A BLAST search of the SwissProt database with the conceptually translated CLN2 candidate gave a highly significant match with PsCP: probability= $1.9 \times 10^{-11}$; the Dayhoff comparison score is > 8 standard deviations above the mean (ALIGN program, relative to 200 comparisons of scrambled sequences); and pairwise comparison using GCG Bestfit yields identity and similarity scores of 25 and 46%, respectively. PsCP is related (52% identical, 66% similar) to XaCP. XaCP is not detected in a BLAST search with the CLN2 candidate, but in pairwise comparisons the Dayhoff comparison score is > 2.7 standard deviations above the mean and the identity and similarity scores are 24 and 48%, respectively.

Analysis of brain autopsy specimens indicate that normal brain contains an acid protease activity not inhibited by pepstatin and E64, while this activity is essentially absent from CLN2 brains (FIG. 4, lower panel). Pepstatin-insensitive carboxyl proteases have not, to date, been reported to exist in mammals, and would thus have been overlooked in earlier biochemical studies of lysosomal activities in LINCL patients. One characteristic of LINCL is the storage of mitochondrial ATP synthase subunit c in the lysosomes of patients (19, 20, 21) which may indicate that subunit c represents a substrate for the CLN2 protein. Also, while the prominent neurological component of LINCL may be due to the susceptibility of neurons to metabolic insults, one intriguing possibility is that the CLN2 protein is involved in processing of neuron-specific trophic factors.

REFERENCES

1. R-.M. Boustany, *Neurodystrophies and Neurolipidoses*. H. W. Moser, Ed., Handbook of Clinical Neurology (Elsevier Science, Amsterdam, 1996), vol. 22(66), pp. 671-700.
2. J. A. Rider, G. Dawson, A. N. Siakotos, *American Journal of Medical Genetics* 42, 519-24 (1992).
3. J. D. Sharp, et al., *Human Molecular Genetics* 6, 591-5 (1997).
4. J. Vesa, et al., *Nature* 376, 584-7 (1995).
5. T. I. B. D. Consortium, *Cell* 82, 949-57 (1995).
6. G. O. Ivy, F. Schottler, J. Wertzel, M. Baudry, G. Lynch, *Science* 226, 985-7 (1984).
7. G. O. Ivy. *American Journal of Medical Genetics* 42, 555-60 (1992).
8. S. Kornfeld. W. S. Sly, *The Metabolic and molecular bases of inherited disease*. C. R. Sciver. A. L. Beaudet, W. S. Sly, D. Valle. Eds. (McGraw-Hill, Inc., New York, 1995), vol. II. pp. 2495-2508.
9. D. E. Sleat, I. Sonar. H. Lackland, J. Majercak, P. Lobel, *Journal of Biological Chemistry* 271, 19191-8 (1996).
10. D. E. Sleat, S. R. Kraus. I. Sonar, H. Lackland, P. Lobel, *Biochemical Journal* 324, 33-39 (1997).
11. K. J. Valenzano, L. M. Kallay. P. Lobel, *Analytical Biochemistry* 209, 156-62 (1993).
17. K. Oda, T. Takahashi, Y. Tokuda, Y. Shibano, S. Takahashi, *Journal of Biological Chemistry* 269, 26518-24 (1994).
18. K. Oda, et al., *Journal of Biochemistry* 120, 564-72 (1996).
19. D. N. Palmer, I. M. Fearnley, S. M. Medd, *American Journal of Medical Genetics* 42, 561-567 (1992).
20. D. N. Palmer, et al., *Journal of Biological Chemistry* 264, 5736-40 (1989).
21. J. Ezaki, L. S. Wolfe, E. Kominami, *Journal of Neurochemistry* 67, 1677-1687 (1996).

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A method for diagnosis for Late Infantile Neuronal Ceroid Lipofuscinosis (LINCL) comprising:
   (a) obtaining a biological sample from a subject to be diagnosed;
   (b) measuring the amount of CLN2 pepstatin-insensitive carboxyl protease activity in the biological sample; and
   (c) comparing the amount of CLN2 pepstatin-insensitive carboxyl protease activity obtained from step (b) with the amount of CLN2 pepstatin-insensitive carboxyl protease activity in a biological sample from a normal control subject, wherein a lower amount of CLN2 pepstatin-insensitive carboxyl protease activity obtained from step (b) than the amount obtained from the normal control subject is indicative of the presence of LINCL.

2. The method of claim 1, wherein the biological sample is blood.

3. The method of claim 1, wherein the CLN2 pepstatin-insensitive carboxyl protease activity is measured using a CLN2 substrate, pepstatin, E-64, and fluorescamine.

4. The method of claim 3, wherein the CLN2 substrate is bovine hemoglobin.

5. A method for diagnosis for Late Infantile Neuronal Ceroid Lipofuscinosis (LINCL) comprising:
   (a) obtaining a biological sample from a subject to be diagnosed; and
   (b) measuring the amount of CLN2 protease activity in the biological sample;
   wherein a lack of CLN2 protease activity or a lower amount of CLN2 protease activity obtained from step (b) than the amount of CLN2 protease activity in a biological sample from a normal control subject is indicative of the presence of LINCL.

* * * * *

UNITED STATES PATENT AND TRADEMARK OFFICE
CERTIFICATE OF CORRECTION

PATENT NO. : 7,745,166 B2  
APPLICATION NO. : 12/175427  
DATED : June 29, 2010  
INVENTOR(S) : Peter Lobel et al.

It is certified that error appears in the above-identified patent and that said Letters Patent is hereby corrected as shown below:

Column 1, line 15, delete the phrase "and NS30147" and insert the phrase -- NS30147 and NS037918 -- after the phrase "National Institutes of Health Grants DK45992" to read:

-- National Institutes of Health Grants DK45992, NS30147 and NS037918 --.

Signed and Sealed this  
Twenty-third Day of October, 2012

David J. Kappos  
*Director of the United States Patent and Trademark Office*

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:

(A) LENGTH: 3487 base pairs
(B) TYPE: nucleic acid
(C) STRANDEDNESS: double
(D) TOPOLOGY: linear (ii) MOLECULE TYPE: cDNA (iii) HYPOTHETICAL: NO (xi) SEQUENCE DESCRIPTION: SEQ ID NO: 1:

```
CGCGGAAGGG CAGAATGGGA CTCCAAGCCT GCCTCCTAGG GCTCTTTGCC CTCATCCTCT      60
CTGGCAAATG CAGTTACAGC CCGGAGCCCG ACCAGCGGAG GACGCTGCCC CCAGGCTGGG     120
TGTCCCTGGG CCGTGCGGAC CCTGAGGAAG AGCTGAGTCT CACCTTTGCC CTGAGACAGC     180
AGAATGTGGA AAGACTCTCG GAGCTGGTGC AGGCTGTGTC GGATCCCAGC TCTCCTCAAT     240
ACGGAAAATA CCTGACCCTA GAGAATGTGG CTGATCTGGT GAGGCCATCC CCACTGACCC     300
TCCACACGGT GCAAAAATGG CTCTTGGCAG CCGGAGCCCA GAAGTGCCAT TCTGTGATCA     360
CACAGGACTT TCTGACTTGC TGGCTGAGCA TCCGACAAGC AGAGCTGCTG CTCCCTGGGG     420
CTGAGTTTCA TCACTATGTG GGAGGACCTA CGGAAACCCA TGTTGTAAGG TCCCCACATC     480
CCTACCAGCT TCCACAGGCC TTGGCCCCCC ATGTGGACTT TGTGGGGGGA CTGCACCATT     540
TTCCCCCAAC ATCATCCCTG AGGCAACGTC CTGAGCCGCA GGTGACAGGG ACTGTAGGCC     600
TGCATCTGGG GGTAACCCCC TCTGTGATCC GTAAGCGATA CAACTTGACC TCACAAGACG     660
TGGGCTCTGG CACCAGCAAT AACAGCCAAG CCTGTGCCCA GTTCCTGGAG CAGTATTTCC     720
ATGACTCAGA CCTGGCTCAG TTCATGCGCC TCTTCGGTGG CAACTTTGCA CATCAGGCAT     780
CAGTAGCCCG TGTGGTTGGA CAACAGGGCC GGGGCCGGGC CGGGATTGAG GCCAGTCTAG     840
ATGTGCAGTA CCTGATGAGT GCTGGTGCCA ACATCTCCAC CTGGGTCTAC AGTAGCCCTG     900
GCCGGCATGA GGGACAGGAG CCCTTCCTGC AGTGGCTCAT GCTGCTCAGT AATGAGTCAG     960
CCCTGCCACA TGTGCATACT GTGAGCTATG AGATGATGA GGACTCCCTC AGCAGCGCCT    1020
ACATCCAGCG GGTCAACACT GAGCTCATGA AGGCTGCTGC TCGGGGTCTC ACCCTGCTCT    1080
TCGCCTCAGG TGACAGTGGG GCCGGGTGTT GGTCTGTCTC TGGAAGACAC CAGTTCCGCC    1140
CTACCTTCCC TGCCTCCAGC CCCTATGTCA CCACAGTGGG AGGCACATCC TTCCAGGAAC    1200
CTTTCCTCAT CACAAATGAA ATTGTTGACT ATATCAGTGG TGGTGGCTTC AGCAATGTGT    1260
TCCCACGGCC TTCATACCAG GAGGAAGCTG TAACGAAGTT CCTGAGCTCT AGCCCCCACC    1320
TGCCACCATC CAGTTACTTC AATGCCAGTG GCCGTGCCTA CCCAGATGTG GCTGCACTTT    1380
CTGATGGCTA CTGGGTGGTC AGCAACAGAG TGCCCATTCC ATGGGTGTCC GGAACCTCGG    1440
CCTCTACTCC AGTGTTTGGG GGGATCCTAT CCTTGATCAA TGAGCACAGG ATCCTTAGTG    1500
GCCGCCCCCC TCTTGGCTTT CTCAACCCAA GGCTCTACCA GCAGCATGGG GCAGGACTCT    1560
TTGATGTAAC CCGTGGCTGC CATGAGTCCT GTCTGGATGA AGAGGTAGAG GGCCAGGGTT    1620
TCTGCTCTGG TCCTGGCTGG GATCCTGTAA CAGGCTGGGG AACACCCAAC TTCCCAGCTT    1680
TGCTGAAGAC TCTACTCAAC CCCTGACCCT TTCCTATCAG GAGAGATGGC TTGTCCCCTG    1740
CCCTGAAGCT GGCAGTTCAG TCCCTTATTC TGCCCTGTTG GAAGCCCTGC TGAACCCTCA    1800
ACTATTGACT GCTGCAGACA GCTTATCTCC CTAACCCTGA AATGCTGTGA GCTTGACTTG    1860
ACTCCCAACC CTACCATGCT CCATCATACT CAGGTCTCCC TACTCCTGCC TTAGATTCCT    1920
CAATAAGATG CTGTAACTAG CATTTTTTGA ATGCCTCTCC CTCCGCATCT CATCTTTCTC    1980
TTTTCAATCA GGCTTTTCCA AAGGGTTGTA TACAGACTCT GTGCACTATT TCACTTGATA    2040
```

-continued

```
TTCATTCCCC AATTCACTGC AAGGAGACCT CTACTGTCAC CGTTTACTCT TTCCTACCCT    2100
GACATCCAGA AACAATGGCC TCCAGTGCAT ACTTCTCAAT CTTTGCTTTA TGGCCTTTCC    2160
ATCATAGTTG CCCACTCCCT CTCCTTACTT AGCTTCCAGG TCTTAACTTC TCTGACTACT    2220
CTTGTCTTCC TCTCTCATCA ATTTCTGCTT CTTCATGGAA TGCTGACCTT CATTGCTCCA    2280
TTTGTAGATT TTTGCTCTTC TCAGTTTACT CATTGTCCCC TGGAACAAAT CACTGACATC    2340
TACAACCATT ACCATCTCAC TAAATAAGAC TTTCTATCCA ATAATGATTG ATACCTCAAA    2400
TGTAAGATGC GTGATACTCA ACATTTCATC GTCCACCTTC CCAACCCCAA ACAATTCCAT    2460
CTCGTTTCTT CTTGGTAAAT GATGCTATGC TTTTTCCAAC CAAGCCAGAA ACCTGTGTCA    2520
TCTTTTCACC CCACCTTCAA TCAACAAGTC CTCAATCAAC AAGTCCTACT GACTGCACAT    2580
CTTAAATATA TCTTTATCAG TCCACAAGTC CTTCCAATTA TATTTCCCAA GTATATCTAG    2640
AACTTATCCA CTTATATCCC CACTGCTACT ACCTTAGTTT AGGGCTATAT TCTCTTGAAA    2700
AAAAGTGTCC TTACTTCCTG CCAATCCCCA AGTCATCTTC CAGAGTAAAA TGCAAATCCC    2760
ATCAGGCCAC TTGGATGAAA ACCCTTCAAG GATTACTGGA TAGAATTCAG GCTTTCCCCT    2820
CCASCCCCCA ATCATAGCTC ACAAACCTTC CTTGCTATTT GTTCTTAAGT AAAAAATCAT    2880
TTTTCCTCCT CCCTCCCCAA ACCCCAAGGA ACTCTCACTC TTGCTCAAGC TGTTCCGTCC    2940
CCTTACCACC CCTGATACAA CTGCCAGGTT AATTTCCAGA ATTCTTGCAA GACTCAGTTC    3000
AGAAGTCACC TTCTTTCGTG AATGTTTTGA TTCCCTGAGG CTACTTTATT TTGGTATGGC    3060
TGAAAAATCC TAGATTTTCT AAACAAAACC TGTTTGAATC TTGGTTCTGA TATGGACTAG    3120
GAGAGAGACT GGGTCAAGTA AGCTTATCTC CCTGAGGCTG TTTCCTCGTC TGTTAAGTGT    3180
GAATATCAAT ACCTGCCTTT CATAATCACC AGGGAATAAA GTGGAATAAT GTTGATAACA    3240
GTGCTTGGCA CCTGGAAGTA GGTGGCAGAT GTTAACGCCC TTCCTCCCTT GCACTGCGCC    3300
CCCTGTGCCT ACCTCTAGCA TTGTAACGAC CACATAGTAT TGAAATGGCC AGTTTACTTG    3360
TCTGCCTTCC TTTCCAAGAC CGTTGGTGCC TAGAGGACTA GAATCGTGTC CTATTTAACT    3420
TTGTGTTCCC AGGTCCTAGC TCAGGAGTTG GCAAATAAGA ATTAAATGTC TGCTACACCG    3480
AAACAAA                                                              3487
```

(2) INFORMATION FOR SEQ ID NO: 2:

(i) SEQUENCE CHARACTERISTICS:
        (A) LENGTH: 2520 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO: 2:

```
CGCGGAAGGG CAGAATGGGA CTCCAAGCCT GCCTCCTAGG GCTCTTTGCC CTCATCCTCT      60
CTGGCAAATG CAGTTACAGC CCGGAGCCCG ACCAGCGGAG GACGCTGCCC CCAGGCTGGG     120
TGTCCCTGGG CCGTGCGGAC CCTGAGGAAG AGCTGAGTCT CACCTTTGCC CTGAGACAGC     180
AGAATGTGGA AAGACTCTCG GAGCTGGTGC AGGCTGTGTC GGATCCCAGC TCTCCTCAAT     240
ACGGAAAATA CCTGACCCTA GAGAATGTGG CTGATCTGGT GAGGCCATCC CCACTGACCC     300
TCCACACGGT GCAAAAATGG CTCTTGGCAG CCGGAGCCCA GAAGTGCCAT TCTGTGATCA     360
CACAGGACTT TCTGACTTGC TGGCTGAGCA TCCGACAAGC AGAGCTGCTG CTCCCTGGGG     420
```

-continued

```
CTGAGTTTCA TCACTATGTG GGAGGACCTA CGGAAACCCA TGTTGTAAGG TCCCCACATC      480
CCTACCAGCT TCCACAGGCC TTGGCCCCCC ATGTGGACTT TGTGGGGGGA CTGCACCATT      540
TTCCCCCAAC ATCATCCCTG AGGCAACGTC CTGAGCCGCA GGTGACAGGG ACTGTAGGCC      600
TGCATCTGGG GGTAACCCCC TCTGTGATCC GTAAGCGATA CAACTTGACC TCACAAGACG      660
TGGGCTCTGG CACCAGCAAT AACAGCCAAG CCTGTGCCCA GTTCCTGGAG CAGTATTTCC      720
ATGACTCAGA CCTGGCTCAG TTCATGCGCC TCTTCGGTGG CAACTTTGCA CATCAGGCAT      780
CAGTAGCCCG TGTGGTTGGA CAACAGGGCC GGGGCCGGGC CGGGATTGAG GCCAGTCTAG      840
ATGTGCAGTA CCTGATGAGT GCTGGTGCCA ACATCTCCAC CTGGGTCTAC AGTAGCCCTG      900
GCCGGCATGA GGGACAGGAG CCCTTCCTGC AGTGGCTCAT GCTGCTCAGT AATGAGTCAG      960
CCCTGCCACA TGTGCATACT GTGAGCTATG GAGATGATGA GGACTCCCTC AGCAGCGCCT     1020
ACATCCAGCG GGTCAACACT GAGCTCATGA AGGCTGCTGC TCGGGGTCTC ACCCTGCTCT     1080
TCGCCTCAGG TGACAGTGGG GCCGGGTGTT GGTCTGTCTC TGGAAGACAC CAGTTCCGCC     1140
CTACCTTCCC TGCCTCCAGC CCCTATGTCA CCACAGTGGG AGGCACATCC TTCCAGGAAC     1200
CTTTCCTCAT CACAAATGAA ATTGTTGACT ATATCAGTGG TGGTGGCTTC AGCAATGTGT     1260
TCCCACGGCC TTCATACCAG GAGGAAGCTG TAACGAAGTT CCTGAGCTCT AGCCCCCACC     1320
TGCCACCATC CAGTTACTTC AATGCCAGTG GCCGTGCCTA CCCAGATGTG GCTGCACTTT     1380
CTGATGGCTA CTGGGTGGTC AGCAACAGAG TGCCCATTCC ATGGGTGTCC GGAACCTCGG     1440
CCTCTACTCC AGTGTTTGGG GGGATCCTAT CCTTGATCAA TGAGCACAGG ATCCTTAGTG     1500
GCCGCCCCCC TCTTGGCTTT CTCAACCCAA GGCTCTACCA GCAGCATGGG GCAGGACTCT     1560
TTGATGTAAC CCGTGGCTGC CATGAGTCCT GTCTGGATGA AGAGGTAGAG GGCCAGGGTT     1620
TCTGCTCTGG TCCTGGCTGG GATCCTGTAA CAGGCTGGGG AACACCCAAC TTCCCAGCTT     1680
TGCTGAAGAC TCTACTCAAC CCCTGACCCT TTCCTATCAG GAGAGATGGC TTGTCCCCTG     1740
CCCTGAAGCT GGCAGTTCAG TCCCTTATTC TGCCCTGTTG GAAGCCCTGC TGAACCCTCA     1800
ACTATTGACT GCTGCAGACA GCTTATCTCC CTAACCCTGA AATGCTGTGA GCTTGACTTG     1860
ACTCCCAACC CTACCATGCT CCATCATACT CAGGTCTCCC TACTCCTGCC TTAGATTCCT     1920
CAATAAGATG CTGTAACTAG CATTTTTTGA ATGCCTCTCC CTCCGCATCT CATCTTTCTC     1980
TTTTCAATCA GGCTTTTCCA AAGGGTTGTA TACAGACTCT GTGCACTATT TCACTTGATA     2040
TTCATTCCCC AATTCACTGC AAGGAGACCT CTACTGTCAC CGTTTACTCT TTCCTACCCT     2100
GACATCCAGA AACAATGGCC TCCAGTGCAT ACTTCTCAAT CTTTGCTTTA TGGCCTTTCC     2160
ATCATAGTTG CCCACTCCCT CTCCTTACTT AGCTTCCAGG TCTTAACTTC TCTGACTACT     2220
CTTGTCTTCC TCTCTCATCA ATTTCTGCTT CTTCATGGAA TGCTGACCTT CATTGCTCCA     2280
TTTGTAGATT TTTGCTCTTC TCAGTTTACT CATTGTCCCC TGGAACAAAT CACTGACATC     2340
TACAACCATT ACCATCTCAC TAAATAAGAC TTTCTATCCA ATAATGATTG ATACCTCAAA     2400
TGTAAGATGC GTGATACTCA ACATTTCATC GTCCACCTTC CCAACCCCAA ACAATTCCAT     2460
CTCGTTTCTT CTTGGTAAAT GATGCTATGC TTTTTCCAAC CAAAAAAAAA AAAAAAAAA      2520
```

(2) INFORMATION FOR SEQ ID NO: 3:

(i) SEQUENCE CHARACTERISTICS:
        (A) LENGTH: 563 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO: 3:

```
Met Gly Leu Gln Ala Cys Leu Leu Gly Leu Phe Ala Leu Ile Leu Ser
1               5                   10                  15

Gly Lys Cys Ser Tyr Ser Pro Glu Pro Asp Gln Arg Arg Thr Leu Pro
                20                  25                  30

Pro Gly Trp Val Ser Leu Gly Arg Ala Asp Pro Glu Glu Glu Leu Ser
            35                  40                  45

Leu Thr Phe Ala Leu Arg Gln Gln Asn Val Glu Arg Leu Ser Glu Leu
        50                  55                  60

Val Gln Ala Val Ser Asp Pro Ser Ser Pro Gln Tyr Gly Lys Tyr Leu
65                  70                  75                  80

Thr Leu Glu Asn Val Ala Asp Leu Val Arg Pro Ser Pro Leu Thr Leu
                85                  90                  95

His Thr Val Gln Lys Trp Leu Leu Ala Ala Gly Ala Gln Lys Cys His
                100                 105                 110

Ser Val Ile Thr Gln Asp Phe Leu Thr Cys Trp Leu Ser Ile Arg Gln
            115                 120                 125

Ala Glu Leu Leu Leu Pro Gly Ala Glu Phe His His Tyr Val Gly Gly
        130                 135                 140

Pro Thr Glu Thr His Val Val Arg Ser Pro His Pro Tyr Gln Leu Pro
145                 150                 155                 160

Gln Ala Leu Ala Pro His Val Asp Phe Val Gly Gly Leu His His Phe
                165                 170                 175

Pro Pro Thr Ser Ser Leu Arg Gln Arg Pro Glu Pro Gln Val Thr Gly
            180                 185                 190

Thr Val Gly Leu His Leu Gly Val Thr Pro Ser Val Ile Arg Lys Arg
        195                 200                 205

Tyr Asn Leu Thr Ser Gln Asp Val Gly Ser Gly Thr Ser Asn Asn Ser
210                 215                 220

Gln Ala Cys Ala Gln Phe Leu Glu Gln Tyr Phe His Asp Ser Asp Leu
225                 230                 235                 240

Ala Gln Phe Met Arg Leu Phe Gly Gly Asn Phe Ala His Gln Ala Ser
                245                 250                 255

Val Ala Arg Val Val Gly Gln Gln Gly Arg Gly Arg Ala Gly Ile Glu
            260                 265                 270

Ala Ser Leu Asp Val Gln Tyr Leu Met Ser Ala Gly Ala Asn Ile Ser
        275                 280                 285

Thr Trp Val Tyr Ser Ser Pro Gly Arg His Glu Gly Gln Glu Pro Phe
        290                 295                 300

Leu Gln Trp Leu Met Leu Leu Ser Asn Glu Ser Ala Leu Pro His Val
305                 310                 315                 320

His Thr Val Ser Tyr Gly Asp Asp Glu Asp Ser Leu Ser Ser Ala Tyr
                325                 330                 335

Ile Gln Arg Val Asn Thr Glu Leu Met Lys Ala Ala Ala Arg Gly Leu
            340                 345                 350

Thr Leu Leu Phe Ala Ser Gly Asp Ser Gly Ala Gly Cys Trp Ser Val
        355                 360                 365

Ser Gly Arg His Gln Phe Arg Pro Thr Phe Pro Ala Ser Ser Pro Tyr
        370                 375                 380

Val Thr Thr Val Gly Gly Thr Ser Phe Gln Glu Pro Phe Leu Ile Thr
```

-continued

```
            385                 390                 395                 400
Asn Glu Ile Val Asp Tyr Ile Ser Gly Gly Phe Ser Asn Val Phe
                405                 410                 415

Pro Arg Pro Ser Tyr Gln Glu Ala Val Thr Lys Phe Leu Ser Ser
                420                 425                 430

Ser Pro His Leu Pro Pro Ser Tyr Phe Asn Ala Ser Gly Arg Ala
                435                 440                 445

Tyr Pro Asp Val Ala Ala Leu Ser Asp Gly Tyr Trp Val Val Ser Asn
            450                 455                 460

Arg Val Pro Ile Pro Trp Val Ser Gly Thr Ser Ala Ser Thr Pro Val
465                 470                 475                 480

Phe Gly Gly Ile Leu Ser Leu Ile Asn Glu His Arg Ile Leu Ser Gly
                485                 490                 495

Arg Pro Pro Leu Gly Phe Leu Asn Pro Arg Leu Tyr Gln Gln His Gly
                500                 505                 510

Ala Gly Leu Phe Asp Val Thr Arg Gly Cys His Glu Ser Cys Leu Asp
                515                 520                 525

Glu Glu Val Glu Gly Gln Gly Phe Cys Ser Gly Pro Gly Trp Asp Pro
                530                 535                 540

Val Thr Gly Trp Gly Thr Pro Asn Phe Pro Ala Leu Leu Lys Thr Leu
545                 550                 555                 560

Leu Asn Pro (2) INFORMATION FOR SEQ ID NO: 4:

(i) SEQUENCE CHARACTERISTICS:
          (A) LENGTH: 587 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO: 4:

Met Lys Ser Ser Ala Ala Lys Gln Thr Val Leu Cys Leu Asn Arg Tyr
1               5                   10                  15

Ala Val Val Ala Leu Pro Leu Ala Ile Ala Ser Phe Ala Ala Phe Gly
                20                  25                  30

Ala Ser Pro Ala Ser Thr Leu Trp Ala Pro Thr Asp Thr Lys Ala Phe
                35                  40                  45

Val Thr Pro Ala Gln Val Glu Ala Arg Ser Ala Ala Pro Leu Leu Glu
            50                  55                  60

Leu Ala Ala Gly Glu Thr Ala His Ile Val Val Ser Leu Lys Leu Arg
65              70                  75                  80

Asp Glu Ala Gln Leu Lys Gln Leu Ala Gln Ala Val Asn Gln Pro Gly
                85                  90                  95

Asn Ala Gln Phe Gly Lys Phe Leu Lys Arg Arg Gln Phe Leu Ser Gln
                100                 105                 110

Phe Ala Pro Thr Glu Ala Gln Val Gln Ala Val Val Ala His Leu Arg
                115                 120                 125

Lys Asn Gly Phe Val Asn Ile His Val Val Pro Asn Arg Leu Leu Ile
                130                 135                 140

Ser Ala Asp Gly Ser Ala Gly Ala Val Lys Ala Ala Phe Asn Thr Pro
145             150                 155                 160
```

-continued

```
Leu Val Arg Tyr Gln Leu Asn Gly Lys Ala Gly Tyr Ala Asn Thr Ala
                165                 170                 175

Pro Ala Gln Val Pro Gln Asp Leu Gly Glu Ile Val Gly Ser Val Leu
            180                 185                 190

Gly Leu Gln Asn Val Thr Arg Ala His Pro Met Leu Lys Val Gly Glu
        195                 200                 205

Arg Ser Ala Ala Lys Thr Leu Ala Ala Gly Thr Ala Lys Gly His Asn
    210                 215                 220

Pro Thr Glu Phe Pro Thr Ile Tyr Asp Ala Ser Ser Ala Pro Thr Ala
225                 230                 235                 240

Ala Asn Thr Thr Val Gly Ile Ile Thr Ile Gly Gly Val Ser Gln Thr
                245                 250                 255

Leu Gln Asp Leu Gln Gln Phe Thr Ser Ala Asn Gly Leu Ala Ser Val
            260                 265                 270

Asn Thr Gln Thr Ile Gln Thr Gly Ser Ser Asn Gly Asp Tyr Ser Asp
        275                 280                 285

Asp Gln Gln Gly Gln Gly Glu Trp Asp Leu Asp Ser Gln Ser Ile Val
    290                 295                 300

Gly Ser Ala Gly Gly Ala Val Gln Gln Leu Leu Phe Tyr Met Ala Asp
305                 310                 315                 320

Gln Ser Ala Ser Gly Asn Thr Gly Leu Thr Gln Ala Phe Asn Gln Ala
                325                 330                 335

Val Ser Asp Asn Val Ala Lys Val Ile Asn Val Ser Leu Gly Trp Cys
            340                 345                 350

Glu Ala Asp Ala Asn Ala Asp Gly Thr Leu Gln Ala Glu Asp Arg Ile
        355                 360                 365

Phe Ala Thr Ala Ala Gln Gly Gln Thr Phe Ser Val Ser Ser Gly
    370                 375                 380

Asp Glu Gly Val Tyr Glu Cys Asn Asn Arg Gly Tyr Pro Asp Gly Ser
385                 390                 395                 400

Thr Tyr Ser Val Ser Trp Pro Ala Ser Ser Pro Asn Val Ile Ala Val
                405                 410                 415

Gly Gly Thr Thr Leu Tyr Thr Thr Ser Ala Gly Ala Tyr Ser Asn Glu
            420                 425                 430

Thr Val Trp Asn Glu Gly Leu Asp Ser Asn Gly Lys Leu Trp Ala Thr
        435                 440                 445

Gly Gly Gly Tyr Ser Val Tyr Glu Ser Lys Pro Ser Trp Gln Ser Val
    450                 455                 460

Val Ser Gly Thr Pro Gly Arg Arg Leu Leu Pro Asp Ile Ser Phe Asp
465                 470                 475                 480

Ala Ala Gln Gly Thr Gly Ala Leu Ile Tyr Asn Tyr Gly Gln Leu Gln
                485                 490                 495

Gln Ile Gly Gly Thr Ser Leu Ala Ser Pro Ile Phe Val Gly Leu Trp
            500                 505                 510

Ala Arg Leu Gln Ser Ala Asn Ser Asn Ser Leu Gly Phe Pro Ala Ala
        515                 520                 525

Ser Phe Tyr Ser Ala Ile Ser Ser Thr Pro Ser Leu Val His Asp Val
    530                 535                 540

Lys Ser Gly Asn Asn Gly Tyr Gly Gly Tyr Gly Tyr Asn Ala Gly Thr
545                 550                 555                 560

Gly Trp Asp Tyr Pro Thr Gly Trp Gly Ser Leu Asp Ile Ala Lys Leu
                565                 570                 575

Ser Ala Tyr Ile Arg Ser Asn Gly Phe Gly His
```

-continued

```
                580                 585

(2) INFORMATION FOR SEQ ID NO: 5:

(i) SEQUENCE CHARACTERISTICS:
        (A) LENGTH: 635 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO: 5:

Met Lys Ile Glu Lys Thr Ala Leu Thr Val Ala Ile Ala Leu Ala Met
1               5                   10                  15

Ser Ser Leu Ser Ala His Ala Glu Asp Ala Trp Val Ser Thr His Thr
            20                  25                  30

Gln Ala Ala Met Ser Pro Pro Ala Ser Thr Gln Val Leu Ala Ala Ser
        35                  40                  45

Ser Thr Ser Ala Thr Thr Thr Gly Asn Ala Tyr Thr Leu Asn Met Thr
    50                  55                  60

Gly Ser Pro Arg Ile Asp Gly Ala Ala Val Thr Ala Leu Glu Ala Asp
65                  70                  75                  80

His Pro Leu His Val Glu Val Ala Leu Lys Leu Arg Asn Pro Asp Ala
                85                  90                  95

Leu Gln Thr Phe Leu Ala Gly Val Thr Thr Pro Gly Ser Ala Leu Phe
            100                 105                 110

Gly Lys Phe Leu Thr Pro Ser Gln Phe Thr Glu Arg Phe Gly Pro Thr
        115                 120                 125

Gln Ser Gln Val Asp Ala Val Ala His Leu Gln Ala Gly Phe
    130                 135                 140

Thr Asn Ile Glu Val Ala Pro Asn Arg Leu Leu Ile Ser Ala Asp Gly
145                 150                 155                 160

Thr Ala Gly Ala Ala Thr Asn Gly Phe Arg Thr Ser Ile Lys Arg Phe
                165                 170                 175

Ser Ala Asn Gly Arg Glu Phe Phe Ala Asn Asp Ala Pro Ala Leu Val
            180                 185                 190

Pro Ala Ser Leu Gly Asp Ser Val Asn Ala Val Leu Gly Leu Gln Asn
        195                 200                 205

Val Ser Val Lys His Thr Leu His His Val Tyr His Pro Glu Asp Val
    210                 215                 220

Thr Val Pro Gly Pro Asn Val Gly Thr Gln Ala Ala Ala Val Ala
225                 230                 235                 240

Ala His His Pro Gln Asp Phe Ala Ala Ile Tyr Gly Gly Ser Ser Leu
                245                 250                 255

Pro Ala Ala Thr Asn Thr Ala Val Gly Ile Ile Thr Trp Gly Ser Ile
            260                 265                 270

Thr Gln Thr Val Thr Asp Leu Asn Ser Phe Thr Ser Gly Ala Gly Leu
        275                 280                 285

Ala Thr Val Asn Ser Thr Ile Thr Lys Val Gly Ser Gly Thr Phe Ala
    290                 295                 300

Asn Asp Pro Asp Ser Asn Gly Glu Trp Ser Leu Asp Ser Gln Asp Ile
305                 310                 315                 320

Val Gly Ile Ala Gly Gly Val Lys Gln Leu Ile Phe Tyr Thr Ser Ala
                325                 330                 335
```

```
Asn Gly Asp Ser Ser Ser Gly Ile Thr Asp Ala Gly Ile Thr Ala
            340                 345                 350

Ser Tyr Asn Arg Ala Val Thr Asp Asn Ile Ala Lys Leu Ile Asn Val
            355                 360                 365

Ser Leu Gly Glu Asp Glu Thr Ala Gln Gln Ser Gly Thr Gln Ala
            370                 375                 380

Ala Asp Asp Ala Ile Phe Gln Gln Ala Val Ala Gln Gly Gln Thr Phe
385                 390                 395                 400

Ser Ile Ala Ser Gly Asp Ala Gly Val Tyr Gln Trp Ser Thr Asp Pro
            405                 410                 415

Thr Ser Gly Ser Pro Gly Tyr Val Ala Asn Ser Ala Gly Thr Val Lys
            420                 425                 430

Ile Asp Leu Thr His Tyr Ser Val Ser Glu Pro Ala Ser Ser Pro Tyr
            435                 440                 445

Val Ile Gln Val Gly Gly Thr Thr Leu Ser Thr Ser Gly Thr Thr Trp
            450                 455                 460

Ser Gly Glu Thr Val Trp Asn Glu Gly Leu Ser Ala Ile Ala Pro Ser
465                 470                 475                 480

Gln Gly Asp Asn Asn Gln Arg Leu Trp Ala Thr Gly Gly Gly Val Ser
            485                 490                 495

Leu Tyr Glu Ala Ala Pro Ser Trp Gln Ser Ser Val Ser Ser Ser Thr
            500                 505                 510

Lys Arg Val Gly Pro Asp Leu Ala Phe Asp Ala Ala Ser Ser Ser Gly
            515                 520                 525

Ala Leu Ile Val Val Asn Gly Ser Thr Glu Gln Val Gly Gly Thr Ser
            530                 535                 540

Leu Ala Ser Pro Leu Phe Val Gly Ala Phe Ala Arg Ile Glu Ser Ala
545                 550                 555                 560

Ala Asn Asn Ala Ile Gly Phe Pro Ala Ser Lys Phe Tyr Gln Ala Phe
            565                 570                 575

Pro Thr Gln Thr Ser Leu Leu His Asp Val Thr Ser Gly Asn Asn Gly
            580                 585                 590

Tyr Gln Ser His Gly Tyr Thr Ala Ala Thr Gly Phe Asp Glu Ala Thr
            595                 600                 605

Gly Phe Gly Ser Phe Asp Ile Gly Lys Leu Asn Thr Tyr Ala Gln Ala
            610                 615                 620

Asn Trp Val Thr Gly Gly Gly Gly Ser Thr
625                 630                 635
```

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO: 6:

GTGATCACAG AATGGCACTT    20

(2) INFORMATION FOR SEQ ID NO: 7:

```
        (i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides"

(iii) HYPOTHETICAL: NO (xi) SEQUENCE DESCRIPTION: SEQ ID NO: 7:

AACATGGGTT TCCGTAGGTC                                                     20

(2) INFORMATION FOR SEQ ID NO: 8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides"

(iii) HYPOTHETICAL: NO (xi) SEQUENCE DESCRIPTION: SEQ ID NO: 8:

CTTCCTCAGG GTCCGCACGG                                                     20

(2) INFORMATION FOR SEQ ID NO: 9:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides"

(iii) HYPOTHETICAL: NO (xi) SEQUENCE DESCRIPTION: SEQ ID NO: 9:

TGTAAAACGA CGGCCAGTCA GACCTTCCAG TAGGGACC                                  38

(2) INFORMATION FOR SEQ ID NO: 10:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides"

(iii) HYPOTHETICAL: NO (xi) SEQUENCE DESCRIPTION: SEQ ID NO: 10:

CAGGAAACAG CTATGACCCT GTATCCCACA CAAGAGAT                                  38

(2) INFORMATION FOR SEQ ID NO: 11:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: other nucleic acid
```

-continued

```
        (A) DESCRIPTION: /desc = "Oligonucleotides"

(iii) HYPOTHETICAL: NO (xi) SEQUENCE DESCRIPTION: SEQ ID NO: 11:

TGTAAAACGA CGGCCAGTTA GATGCCATTG GGGACTGG                              38

(2) INFORMATION FOR SEQ ID NO: 12:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO: 12:

CAGGAAACAG CTATGACCGT CATGGAAATA CTGCTCCA                              38
```